(12) United States Patent
Kürnsteiner et al.

(10) Patent No.: US 7,553,635 B2
(45) Date of Patent: Jun. 30, 2009

(54) PROCESS FOR PRODUCTION OF CEPHALOSPORIN C

(75) Inventors: Hubert Kürnsteiner, Angerberg (AT); Ernst Friedlin, Langkampfen (AT)

(73) Assignee: Sandoz AG, Basel (CH)

( * ) Notice: Subject to any disclaimer, the term of this patent is extended or adjusted under 35 U.S.C. 154(b) by 341 days.

(21) Appl. No.: 10/527,552

(22) PCT Filed: Sep. 16, 2003

(86) PCT No.: PCT/EP03/10289

§ 371 (c)(1), (2), (4) Date: Mar. 11, 2005

(87) PCT Pub. No.: WO2004/026902

PCT Pub. Date: Apr. 1, 2004

(65) Prior Publication Data

US 2006/0105424 A1   May 18, 2006

(30) Foreign Application Priority Data

Sep. 17, 2002 (AT) ............................. A 1397/2002

(51) Int. Cl.
*C12P 35/06* (2006.01)
*C12N 15/55* (2006.01)
*C12N 9/16* (2006.01)
*C12N 15/80* (2006.01)
*C12N 1/16* (2006.01)

(52) U.S. Cl. .................. 435/49; 536/23.2; 435/320.1; 435/252.3; 435/325; 435/254.11; 435/196

(58) Field of Classification Search .................. None
See application file for complete search history.

(56) References Cited

OTHER PUBLICATIONS

Connerton et al., "An Acetate-Sensitive Mutant of Neurospora-Crassa Deficient in Acetyl-Coa Hydrolase", Journal of General Microbiology, vol. 138, No. 9, pp. 1797-1800 (1992).

Malmberg et al., "Identification of Rate-Limiting Steps in Cephalosporin C Biosynthesis in Cephalosporium Acremonium: A Theoretical Analysis", Applied Microbiology and Biotechnology, vol. 38, No. 1, pp. 122-128 (1992).

Marathe et al., "Duplication-Induced Mutation of a New Neurospora Gene Required for Acetate Utilization Properties of the Mutant and Predicted AMino Acid Sequence of the Protein Product", Molecular and Cellular Biology, vol. 10, No. 6, pp. 2638-2644 (1990).

Shen et al., "Levels of Isopenicillin N Synthetase and Deacetoxycephalosporin C Synthetase in Cephalosporium-Acremonium Producing High and Low Levels of Cephalosporin C", Bio-Technology, vol. 4, No. 1, pp. 61-62 (1986).

Skatrud et al, "Use of Recombinant DNA to Improve Production of Cephalosporin C by Cephalosporium-Acremonium", Bio-Technology, vol. 7, No. 5, pp. 477-485 (1989).

Ullan et al., "A Novel Epimerization System in Fugal Secondary Metabolism Involved in the Conversation of Isopenicillin N into Penicillin N in Acremonium Chrysogenum", Journal of Biological Chemistry, vol. 277, No. 48, pp. 46216-46225 (2002).

Knihinicki et al., Chiral Inversion of 2-Arylpropionic Acid Non-Steroidal Anti-inflammatory Drugs-II, Racemization and Hydrolysis of (R)- and (S)-Ibuprofen-CoA Thioesters, Biochem. Pharmacol., 1991, vol. 42, No. 10, pp. 1905-1911.

Shieh et al., Purification and Characterization of Novel "2-Arylpropionyl-CoA Epimerases" from Rat Liver Cytosol and Mitochondria, J. Biol. Chem., 1993, vol. 268; No. 5, pp. 3487-3493.

*Primary Examiner*—Rebecca Prouty

(74) *Attorney, Agent, or Firm*—Luedeka, Neely & Graham, P.C.

(57) ABSTRACT

The present invention relates to isolated nucleic acid molecules which code for a new protein from *Acremonium chrysogenum*, to vectors which comprise such a nucleic acid molecule, to *Acremonium chrysogenum* host cells which have been transformed with such a vector and to a method for production of cephalosporin C using such transformed host cells.

22 Claims, 18 Drawing Sheets

Figure 1 (SEQ ID NO 1): Amino acid sequence of the A. chrysogenum protein encoded by a nucleic acid molecule of the invention (depicted from the N terminus to the C terminus)

```
MASPIASAAL KARIRRPSML KKLCKPQDLM HHFPNGSYIG WSGFTGVGYP KKMPTYMADH
VEQNGLQGKL KYSLFVGASS GAETENRWAS LDMIDRRTPH QVGKAISKGI NEGKIHFFDK
HLSMFPVDLV YGYYTKDRPH NKLDVVVVEA TDIKEDGSIV PGASVGATPE LIQMADKIII
EVNTSLPSFE GLHDITMTDL PPLRKPYLVM GVEDRIGRTS IPIDPEKVVG ILESDYQDAT
APNAEADESA NKIAGHLIEF FEHEVAHGRL PNSLLPLQSG IGNVANAIIG GLDNSNFRNL
KVWTEVIQDT FLDLFDSGRL DFATATSIRF SPDGFRRFYD NWEAYYGKLL LRSQQVSNSP
EIIRRLGVIA MNTPVEVDIY AHANSTCVMG SRMLNGLGGS ADFLRSSKYS IMHTPSTRPS
KTDPHGVSCI VPMCTHIDQT EHDLDVIVTE QGLADVRGLS PRERARVIIK KCAHPVYQPI
LTHYFEKAES DCLRKGWGHE PHLLFNSFDL HKALVEHGSM QKVGQW
```

Figure 2 (SEQ ID NO 2): Genomic DNA sequence of the coding region of a genomic clone of the new A. chrysogenum gene from the translation start codon (ATG) to the last coding codon (TGG). The introns are depicted underlined. A single strand in 5'-to-3' orientation is shown.

```
ATGGCATCAC CAATAGCCTC TGCCGCCCTC AAGGCGCGCA TTCGCCGCCC CTCGATGCTC
AAGAAGCTGT GCAAGCCCCA GGATTTGATG CATCACTTCC CCAATGGCTC GTACATTGGC
TGGTCCGGCT TCACCGGCGT CGGCTACCCG AAGTGAGTTC CACCGTCATC CCGCTCCACA
GTAGGCGCAG CCGGCCCGCT GACAGTCCCC GACAGGAAAA TGCCGACCTA CATGGCCGAT
CACGTCGAGC AGAACGGCCT TCAGGGCAAG CTGAAGTACT CGCTATTCGT GGGCGCATCG
TCGGGTGCTG AGACAGAGAA TCGCTGGGCG TCGCTCGACA TGATTGATAG GAGGACCCCG
CATCAGGTCG GCAAGGCCAT CTCCAAGGGC ATCAATGAGG GCAAGATCCA CTTCTTCGAC
AAGCATCTCT CCATGTTCCC CGTGGACCTT GTATACGTAC GTCAACGATG ATCCCTTGGA
ATGTGCATGT ACTACGAGTA CCTGGCGCTA ACATCCGGTC AGGGCTACTA CACAAAGGAT
AGACCCCACA ACAAGCTGGA CGTGGTGGTG GTGGAGGCCA CCGACATCAA AGAGGACGGA
AGCATTGTAC CCGGAGCTTC AGTCGGCGCG ACCCCCGAGC TCATCCAGAT GGCCGATAAG
GTGAGCAATT TCGATTTCTA GCGGAGGGCG CAGCAGGACC TGACATCTCC CTGTGCAGAT
CATTATCGAG GTCAACACCT CACTGCCTTC ATTCGAGGGT CTCCACGACA TCACCATGAC
CGACCTGCCC CCGCTACGGA AGCCCTATCT CGTCATGGGT GTCGAGGACC GCATCGGCAG
GACCTCTATC CCTATCGACC CCGAGAAGGT TGTAGGCATC CTCGAATCCG ACTACCAGGA
CGCCACTGCC CCCAACGCCG AGGCCGACGA GAGTGCGAAC AAGATTGCTG GCCACTTGAT
TGAGTTCTTC GAGCACGAGG TCGCCCACGG CCGTCTCCCG AACTCCCTCC TTCCCCTCCA
GTCCGGCATC GGCAACGTCG CCAACGCCAT CATCGGTGGC CTCGACAACT CCAACTTCCG
CAACCTCAAG GTCTGGACTG AGGTTATCCA GGACACCTTC CTCGACCTCT TCGACTCGGG
CCGCCTCGAC TTTGCCACGG CCACCTCTAT CCGCTTCTCC CCCGACGGTT TCCGCCGGTT
CTACGACAAC TGGGAGGCCT ACTACGGCAA GCTCCTCCTC CGCAGCCAGC AGGTGTCCAA
CTCGCCCGAG ATCATCCGCC GCCTTGGTGT CATTGCCATG AACACCCCCG TCGAGGTCGA
CATCTACGCC CACGCCAACT CCACCTGCGT CATGGGCTCG CGCATGCTCA ACGGCCTGGG
CGGCTCCGCC GACTTCCTGC GCTCCTCCAA GTACTCTATC ATGCACACCC CGTCCACCCG
CCCCTCCAAG ACCGACCCGC ACGGCGTCTC GTGCATCGTT CCCATGTGCA CCCACATCGA
CCAGACTGAG CACGACCTCG ACGTCATCGT CACCGAGCAG GGCCTGGCCG ACGTGCGCGG
CCTGAGCCCC AGGGAGAGGG CCCGCGTCAT CATCAAGAAG TGCGCCCACC CGGTCTACCA
GCCCATCCTG ACCCACTACT TTGAGAAGGC CGAGAGCGAC TGCCTACGCA AGGGCTGGGG
CCACGAGCCC CATCTGCTCT TCAACTCGTT TGACCTGCAC AAGGCCCTCG TGGAGCACGG
AAGCATGCAG AAGGTCGGGC AGTGG
```

Figure 3 (SEQ ID NO 3): cDNA sequence of the coding region of the new A. chrysogenum gene from the translation start codon (ATG) to the last coding codon (TGG). A single strand in 5'-to-3' orientation is shown.

```
ATGGCATCAC CAATAGCCTC TGCCGCCCTC AAGGCGCGCA TTCGCCGCCC CTCGATGCTC
AAGAAGCTGT GCAAGCCCCA GGATTTGATG CATCACTTCC CCAATGGCTC GTACATTGGC
TGGTCCGGCT TCACCGGCGT CGGCTACCCG AAGAAAATGC CGACCTACAT GGCCGATCAC
GTCGAGCAGA ACGGCCTTCA GGGCAAGCTG AAGTACTCGC TATTCGTGGG CGCATCGTCG
GGTGCTGAGA CAGAGAATCG CTGGGCGTCG CTCGACATGA TTGATAGGAG GACCCCGCAT
CAGGTCGGCA AGGCCATCTC CAAGGGCATC AATGAGGGCA AGATCCACTT CTTCGACAAG
CATCTCTCCA TGTTCCCCGT GGACCTTGTA TACGGCTACT ACACAAAGGA TAGACCCCAC
AACAAGCTGG ACGTGGTGGT GGTGGAGGCC ACCGACATCA AGAGGACGG AAGCATTGTA
CCCGGAGCTT CAGTCGGCGC GACCCCCGAG CTCATCCAGA TGGCCGATAA GATCATTATC
GAGGTCAACA CCTCACTGCC TTCATTCGAG GGTCTCCACG ACATCACCAT GACCGACCTG
CCCCCGCTAC GGAAGCCCTA TCTCGTCATG GGTGTCGAGG ACCGCATCGG CAGGACCTCT
ATCCCTATCG ACCCCGAGAA GGTTGTAGGC ATCCTCGAAT CCGACTACCA GGACGCCACT
GCCCCCAACG CCGAGGCCGA CGAGAGTGCG AACAAGATTG CTGGCCACTT GATTGAGTTC
TTCGAGCACG AGGTCGCCCA CGGCCGTCTC CCGAACTCCC TCCTTCCCCT CCAGTCCGGC
ATCGGCAACG TCGCCAACGC CATCATCGGT GGCCTCGACA ACTCCAACTT CCGCAACCTC
AAGGTCTGGA CTGAGGTTAT CCAGGACACC TTCCTCGACC TCTTCGACTC GGGCCGCCTC
GACTTTGCCA CGGCCACCTC TATCCGCTTC TCCCCCGACG GTTTCCGCCG GTTCTACGAC
AACTGGGAGG CCTACTACGG CAAGCTCCTC CTCCGCAGCC AGCAGGTGTC CAACTCGCCC
GAGATCATCC GCCGCCTTGG TGTCATTGCC ATGAACACCC CCGTCGAGGT CGACATCTAC
GCCCACGCCA ACTCCACCTG CGTCATGGGC TCGCGCATGC TCAACGGCCT GGGCGGCTCC
GCCGACTTCC TGCGCTCCTC CAAGTACTCT ATCATGCACA CCCCGTCCAC CCGCCCCTCC
AAGACCGACC CGCACGGCGT CTCGTGCATC GTTCCCATGT GCACCCACAT CGACCAGACT
GAGCACGACC TCGACGTCAT CGTCACCGAG CAGGGCCTGG CCGACGTGCG CGGCCTGAGC
CCCAGGGAGA GGGCCCGCGT CATCATCAAG AAGTGCGCCC ACCCGGTCTA CCAGCCCATC
CTGACCCACT ACTTTGAGAA GGCCGAGAGC GACTGCCTAC GCAAGGGCTG GGGCCACGAG
CCCCATCTGC TCTTCAACTC GTTTGACCTG CACAAGGCCC TCGTGGAGCA CGGAAGCATG
CAGAAGGTCG GGCAGTGG
```

Figure 4 (SEQ ID NO 4): Genomic DNA sequence of a BamHI/EcoRI fragment of a genomic clone of the new A. chrysogenum gene (a single strand in 5'-to-3' orientation is shown). The translation start codon (ATG) and the translation stop codon (TAA) of the coding region are depicted underlined and in bold type; the introns are depicted underlined.

```
             GAAG ATCGCATTTG GGCGAGTGGG CTAATAATGC CTGCTGCCTG CCTGTGGACG
GTAAATGAAT TAGGTGGAAT GTGTCGCAAA TTGAGGGGAA TGGCCCCCTT ATCATATAAA
GTGCCAATGC GATACTATGG CGTGGCGTGG GGTCGCGTCG GTGTCCGGCC GGTCGAACGG
AGGTCCCGGC TATCAATAGG CGGTAGGCCG GCATTGAATC GGTTCCACCG TATTCCAGAC
ACCCAAGGAA GGCCCGCCAC CCCCAGCTCC GGCCTGGGGA TAGCGCCGAG TGGAGCACTC
ACGGGGCCG TGTTTGACTC GAAGACGCGT CGTGATTGGC CAGAACTTCA TCCCCCTCTG
CCAAGTATTG GTTCACGGGA TTCGGCGACG TCAACGACCC CACCGGCCCG GATTACATAA
GGTGCACTGC AGCTACTACG TAGTACTCGT ACTTGGGAAG GAGGGACCCT TGGGGTCGGA
GGTTTTAAAG GCAATGGCTT CTTCGCTGGT CCACCCAACC TGACTCTCAC TCTCCCTTTT
ACCTCGCTCC TCTGATTATT CCCTCGTCTG CGTCTGGATT TCATCTCTTT CCCCTCCCGG
CCCCTTTGGA TCTCTGCTCT CCCCTCCTCT CTCCCCGCA TTGGTGTGTA AAACCACTGT
CCCGCGGCCT CGCGACGAGT GACGTACTGC AAGCCGAAAC CTCACAATCC CTTCCTCACA
ATGGCATCAC CAATAGCCTC TGCCGCCCTC AAGGCGCGCA TTCGCCGCCC CTCGATGCTC
AAGAAGCTGT GCAAGCCCCA GGATTTGATG CATCACTTCC CCAATGGCTC GTACATTGGC
TGGTCCGGCT TCACCGGCGT CGGCTACCCG AAGTGAGTTC CACCGTCATC CCGCTCCACA
GTAGGCGCAG CCGGCCCGCT GACAGTCCCC GACAGGAAAA TGCCGACCTA CATGGCCGAT
CACGTCGAGC AGAACGGCCT TCAGGGCAAG CTGAAGTACT CGCTATTCGT GGGCGCATCG
TCGGGTGCTG AGACAGAGAA TCGCTGGGCG TCGCTCGACA TGATTGATAG GAGGACCCCG
CATCAGGTCG GCAAGGCCAT CTCCAAGGGC ATCAATGAGG GCAAGATCCA CTTCTTCGAC
AAGCATCTCT CCATGTTCCC CGTGGACCTT GTATACGTAC GTCAACGATG ATCCCTTGGA
ATGTGCATGT ACTACGAGTA CCTGGCGCTA ACATCCGGTC AGGGCTACTA CACAAAGGAT
AGACCCCACA ACAAGCTGGA CGTGGTGGTG GTGGAGGCCA CCGACATCAA AGAGGACGGA
AGCATTGTAC CCGGAGCTTC AGTCGGCGCG ACCCCCGAGC TCATCCAGAT GGCCGATAAG
GTGAGCAATT TCGATTTCTA GCGGAGGGCG CAGCAGGACC TGACATCTCC CTGTGCAGAT
CATTATCGAG GTCAACACCT CACTGCCTTC ATTCGAGGGT CTCCACGACA TCACCATGAC
CGACCTGCCC CCGCTACGGA AGCCCTATCT CGTCATGGGT GTCGAGGACC GCATCGGCAG
GACCTCTATC CCTATCGACC CCGAGAAGGT TGTAGGCATC CTCGAATCCG ACTACCAGGA
CGCCACTGCC CCCAACGCCG AGGCCGACGA GAGTGCGAAC AAGATTGCTG GCCACTTGAT
TGAGTTCTTC GAGCACGAGG TCGCCCACGG CCGTCTCCCG AACTCCCTCC TTCCCCTCCA
GTCCGGCATC GGCAACGTCG CCAACGCCAT CATCGGTGGC CTCGACAACT CCAACTTCCG
CAACCTCAAG GTCTGGACTG AGGTTATCCA GGACACCTTC CTCGACCTCT TCGACTCGGG
CCGCCTCGAC TTTGCCACGG CCACCTCTAT CCGCTTCTCC CCCGACGGTT TCCGCCGGTT
CTACGACAAC TGGGAGGCCT ACTACGGCAA GCTCCTCCTC CGCAGCCAGC AGGTGTCCAA
CTCGCCCGAG ATCATCCGCC GCCTTGGTGT CATTGCCATG AACACCCCCG TCGAGGTCGA
```

Figure 4 (SEQ ID NO 4) - Continued

```
CATCTACGCC CACGCCAACT CCACCTGCGT CATGGGCTCG CGCATGCTCA ACGGCCTGGG
CGGCTCCGCC GACTTCCTGC GCTCCTCCAA GTACTCTATC ATGCACACCC CGTCCACCCG
CCCCTCCAAG ACCGACCCGC ACGGCGTCTC GTGCATCGTT CCCATGTGCA CCCACATCGA
CCAGACTGAG CACGACCTCG ACGTCATCGT CACCGAGCAG GGCCTGGCCG ACGTGCGCGG
CCTGAGCCCC AGGGAGAGGG CCCGCGTCAT CATCAAGAAG TGCGCCCACC CGGTCTACCA
GCCCATCCTG ACCCACTACT TTGAGAAGGC CGAGAGCGAC TGCCTACGCA AGGGCTGGGG
CCACGAGCCC CATCTGCTCT TCAACTCGTT TGACCTGCAC AAGGCCCTCG TGGAGCACGG
AAGCATGCAG AAGGTCGGGC AGTGGTAAGA TTGGCGAGAC GGGAGAGGCG TTGTTGTAGG
AGTTGGAACT AGAATCAGAT ATACAGCCTT TCATATATGT AGATAATGGA GCCATT
```

Figure 5 (SEQ ID NO 5): A. chrysogenum genomic DNA sequence of an approx. 16 kb region marked by SnaBI and BfrI and containing the biosynthesis genes pcbC (position 1366 to position 350, inverse arrangement) and pcbAB (position 2598 to position 13517). A single strand in 5'-to-3' orientation is shown. The particular translation start codons (ATG, GTG) and the particular translation stop codons (TAA, TGA) of the respective coding regions are depicted underlined and in bold type. The said cleavage sites are depicted underlined.

```
   1    TACGTACATA CGTCGCGGGG GGTAGACAAT GGTGTGGTGT ACGTGTACAA CTACAGTCAG
  61    ACATGGACGC AGGAAACGCA TCATTGATAC ATGCACACGG GGCAGCAAAT TTAGCCTGTT
 121    TCACTACATG TACATAGAGG GTACACTCCA GAGCATACTG ATGGGAGAAA AAGGGTTCGA
 181    TTGCTGGTGG TTTAACATAG CCGGCAAGGG GAAAAAAAAA AGGGGGCGGA GAAGGACTGA
 241    TTCTTCCTGG CAGACACTCG ACCCTTCCGG CCCCTTGAAC TGCTTTTACT CCCGCATTCC
 301    TCCGCACGCC CGCCCACAGC GGCAGATCAG CCGAACCTGA TCGACCGATT TAGGTCTGAC
 361    CATTCTTGTT GATCAAGCCC CGCAGTCCCC CCTGCAGATA CTCTCCGTAG GAGATGGCCG
 421    GCTTGTCCTT GGCGGCATCC TTGGCCCCAT CCTTGGCGGT CGCGGGGTCC CACGGCTGGA
 481    TGGTGTCCTC CCAGCCCAGG TTGACGAAGA AGGGCAGTGA CTGGCGCTCC TCGTTGACCC
 541    ATTTGACGCG GTGGATCGGG GCCGGGTAGT AGTCGTCGGT GATATGGGCC ATGTAGCTGC
 601    CGCAGTTGAT GAGGAAGCCC GTGTCGTCAG CCTGGATGTC CTGCCAGCCC TGCGGGGTCT
 661    TGACCTGCAG ATTCTGCACG TCGGACTGGT ACAACACCGT GATGAGGGAC ACGTCCTCGT
 721    GCCACTCGAA GCTGAGCTTG GTGCCGTCGT CGGCCGTCTT GATGGCCGGC TCCGGGTACG
 781    GGTCGAGGTA CGGGTAACGG ATGAGCACGA CCGACGAGAG CGTCGTGTCA CGGCGGGAGT
 841    GGCGGGTGAA GAAGTCCTCG TCGCGACCTA GGGCGAGAGC GTAGCCGCGC AGCACCGCGG
 901    AGGAGAGGCC GAAGACGTCC CAGTAGTACT TCTCGGCGAA GGCCCGGAAC CCCGGGTGCT
 961    TCGCCTCGTC CGGCCAGACG TTGACCTCGT GCATAGGGGT GGGCTCCTTG ATTCGCGGGT
1021    GGTCTGGGCT GAAGGAGGGG TTCAGGTAGC AGAACGATTC GACCGCCTTC TTGCCCGGGA
1081    TCGGCAGGTA GTAGCCCGCC CGGATCTGGG ACTCGTGCTC CTTGTTGTAG GCCCGGATGG
1141    CGAGCTGCCA CTTCTCCTCG TCCGTGATGC TCATGTGGAA TTTGTTCGTC TCGCGCGAGA
1201    GCCACGGCAG GTCGACACCG TGGTTCACCG CGTAAAAGAA GCCTGTGTCG CGCGATGCGG
1261    CGTCGATGGC GCGAGCTACC TCGAGCTTCT TCTCCTTGTC ATCGCCGAAT AGGGGCGAGA
1321    CATCGATTCG GGGGACGTTG GCCACTGGAA CTGGAACGGA ACCCATGGTG ACGGTTTGTC
1381    CTGCCTGGTG TAAGATGTGA AAGACGAGAT ATGCGTGAGT GACGATGGCG GAAGGAGAAG
1441    CCTCGAAAAT CAGAAGAGCG ACCAAAGGGA TATTCAAGTA TTCGCCCCTC TTGAAGCTGT
1501    TTATACGGGC GGCTGGGTGT GTGTATGTGT ACTTGAGTAC CTACCTCGTG TCTCCCGTTG
1561    CTATACGATA TGAGCTTCCC CACGACGCGC CTTTATGGCC TGACCAAGGT CTCGATTATC
1621    CGGCTCCTGC GGGTGACACT GCCGAGGGGG GTTACATACG GTCCAGCAGC GGCGATGGAG
1681    TTTGGTCCCT GAAGACTGCA TGGCGGGGCC AAGCGATGAG GAACGCCGTT ACATGCATGT
1741    GCATGTAGAC GCCGCCACCC ATGAGGCCCG GAACAGTCTA TCGAAGCTCA GGGATTGGCC
1801    CGGCAACTCG ACGCCCCGTC GAGCGGCTCA CCGGTAGTCG ACGGCGTCCG TCGGAATCTC
1861    GCGCTGCTGC GGGCCACCAC GGCGATGGGC CGTACACACT GCTACTACGG TGTACAATGT
1921    ATCATGTACC CGATCGACGA GGAACTCGGG GTAGAGGTAC CCCGTACAAT CCAGTTTCTC
```

Figure 5 (SEQ ID NO 5) - Continued

```
1981    AACCCAATGG AACCACACAT ACGGGGTGGC TTTGGTTCAC GTTGCACTTT AAACTCGCAG
2041    ACGAGGGACC GACCTGCAGC GTGGCCCACT TCTGAAGCCT GCCCAGCTTT CTGCAAGACG
2101    CGGGCCATCG CGCTTGGCCG AGGAGAGAAA GGGTATCCAT GGCGACAAAG GCGGTCCTGG
2161    TGGGTTCGGT GCCGGCTTTG GAGTTCACTG GTCTGGGTGG GTGGCCAGCT GGATGCATGC
2221    ATTGGCCTGT ATCAAAGGTC CGGGATTCCC CAGGAGTATA AGACGTTCGT GCTGGGAGAT
2281    CTAGCGACGT GTTGGGAAAT ATCGGCCGTA GAGTGCGAAA AAGAACTGGC GGAAATATTT
2341    CTCCTTGGAC TCGGTCACAC TCAGTCAGTA GTGGACTGCC AGTCTATCAT ACACCTTTGA
2401    TATCAACATG ACTATCCTTA CAGGTGCCGA CGACGCCTCG TCATACCACA GGTATGTCTT
2461    CACAGCCTCT GGAAAGCGCA GTTGGGAGCT ATCTCTAACA TTACCACATC AGGCGCAATG
2521    GAAGCTCTGA TATCCCAAAA GGTGCCATCC ACCGCAACGG CTTCGCAGCC GCAGCCCCTG
2581    ACTGCTGGAT CCGGTCCGTG CTGTTTTCCG TGCACCAGAT GCTCAAGAGG TTCGGAAACG
2641    GATCTCACAC CGTCGTGGCG TCACTCGTAA CTTCATCAGA GGGATGCCCT TCAACTTCGG
2701    CCTGGAGGGC CATCCCCTCC GTCATCCATC ATATAGAGGG CGGAGACAAC AACAACACAG
2761    TCGCCTCTGC CGTGGAACAG GCGGCGAATC TCCTGAACTC AGAAGGATCG GGACAGGACC
2821    TTCTGATTCC CATCGGACTC ACTGAGCTCG TCAAGTCGGA GCTGATTGAC CTCCTGGTCA
2881    TCTTCGACGA CGAGACAAAT AACATACGAC TGCCGCAGGA CTTCCCACTT ATCCTGCGGA
2941    TACATCAGCG GCAAGACCAC TGGCAGCTGT CAGTCCGGTA TCCCTCGCCC CTTTTCGACA
3001    CCATGGTCAT CGACAGCTTT CTGAGCGCAC TTCACAACCT GTTGTCCGCG GTGACAAAAC
3061    CCTCCCAGCT CGTGCGCGAC ATCGAGCTGC TCCCAGAATA CCAGGTCGCT CAGCTGGAGA
3121    AGTGGAACAA CACAGACGGC GACTACCCCA CCGAGAAGCG GCTACATCAT CTGTTCGAGG
3181    AGGCAGCAGT GCGTCGTCCC CAACACGTTG CCCTCATCTG CGGCGACAAG CGCATCACCT
3241    ATGAGGAGTT GAATGCTATG GCGAATCGCC TGGCCCACCA TCTGGTATCC TCGGGTATCC
3301    AGACTGAGCA GCTCGTCGGT CTCTTCCTCG ACAAGACCGA GCTCATGATC GCTACTATTC
3361    TGGGCATCTG GAAATCTGGT GCCGCGCATG TACCTATCGA CCCTGGGTAC CCGGACGAGC
3421    GTGTCAAGTT CGTCCTGAAT GATACGAAGG CGCAAGTGGT CATTGCTAGT CAGAGGCACG
3481    TCGATCGACT GCGGGCTGAG GCTGTTGGCG GCCAGCATCT TCGCATCATC GGTCTCGAAT
3541    CTCTGTTCGA CAACCTTGCT CAACAGACAC AACACTCACC AGAGACGTCG GGCAATTTGA
3601    CCCATCTGCC CCTGAACAGC AAACAGCTTG CGTACGTGAC ATACACCTCG GCACCACGG
3661    GCTTCCCGAA AGGCATCTAC AAGGAGCACA CAAGCGTCGT TAACAGCATC ACCGATCTGT
3721    CTGCTCGGTA CGGTGTGGCC GGGGAGGACG ACGAGGTGAT ACTCGTCTTC TCCGCCTACG
3781    TCTTCGAGCC ATTCGTGCGC CAGATGCTCA TGGCCCTGAC CACGGGCAAC TCTCTCGCCA
3841    TCATCAGCGA CGAGGACAAG TTCGACCCTG ACACCCTTAT TCCCTTCATC CAAAAACACA
3901    AAGTCACTTA CATCCACGCC ACCTCGTCAG TGTTGCAGGA GTACGACTTC GGGTCCTGCC
3961    CCTCGTTGAA ACGCATGATT CTGGTGGGAG AGAACTTGAC AGAGCCGCGC TACGAGGCCC
4021    TGAGGCAGCG CTTCAAGTCG CGCATCCTGA ATGAATATGG CTTCACCGAG TCTGCGTTTG
4081    TGACGGCGCT CAACATATTC GAGCCTACCT CACAGAGGAA GGACATGAGT CTGGGAAGGC
4141    CGGTGCGCAA CGTCAAGTGC TATATCTTGG ATGCCAACCT CAAGAGAGTC CCCATCGGTG
4201    TTACAGGGGA GCTGCACATC GGTGGCTTGG GTATATCCCG GGGGTACATG AATAGGGAGG
4261    AGCTCACAAG GCAGAAGTTC CTCCCGAACC CCTACCAGAC CGATAAGGAG CGCCAACGGG
4321    GTGTCAACTC AACCATGTAC AAGACAGGAG ATCTGGCCCG CTGGCTACCC AGTGGCGAAG
4381    TCGAGTATCT CGGCCGTGCC GACTTCCAGA TCAAGCTGCG CGGCATTCGA ATTGAGCCCG
```

Figure 5 (SEQ ID NO 5) - Continued

```
4441   GCGAGATCGA GTCCACTCTC GCCATGTATC CCGGAATCAG GGCCAGCATC GTCGTGTCAA
4501   AGAAGCTTCT CAGTCAGGGG CAGGAGACGA TCCAAGACCA CCTTGTGGGG TACTATGTTT
4561   GCGATGAGGG CCACATCCCC GAGGGTGACC TGCTGAGCTT CCTGGAGAAG AAGCTACCTC
4621   GGTACATGGT CCCGACGCGC CTTGTCCAAC TGGCTCAGAT TCCAACCAAT ATCAACGGCA
4681   AGGCGGATCT GCGTGCTCTT CCTGCCGTCG AAGTCGCCGT AGCTCCCACC CACAAGCAGG
4741   ATGGCGAGCG AGGAAACCAG CTGGAGAGCG ACCTGGCTGC CATATGGGGC AACATTTTGA
4801   GTGTTCCCGC TCAAGACATT GGGTCTGAAT CCAACTTCTT CCGCCTGGGT GGCCACAGTA
4861   TTGCATGCAT CCAGCTCATT GCTCGTGTGC GACAGCAGCT AGGCCAGGGG ATTACCCTCG
4921   AGGAGGTCTT CCAGACCAAG ACGTTGCGAG CTATGGCTGC CCTCTTGTCG AAAAGTACA
4981   CGAAGGCGTC GAATGGGACG AACGGAGTGA CCAACGGCAC TGCTCACGTC AACGGCCACG
5041   CAGCGAACGG CCATGTCAGC GACAGCTACG TGGCCAGCAG TTTGCAGCAA GGCTTTGTTT
5101   ACCATTCACT CAAGAACGAA CTGTCCGAGG CGTACACCAT GCAATCCATG ATCCACTATG
5161   GTGTGCCCCT GAAACGGGAT ATTTACCAAG CGGCATGGCA GAGGGTACAG GGGGAGCACC
5221   CTGCACTGCG GCTTCGGTTC ACATGGGAGG CCGAAGTGAT GCAGATCGTG GACCCGAAAT
5281   CTGAACTCGA CTGGCGTGTT GTTGACTGGA CCGATGTTTC GAGCCGGGAG AAGCAGCTGG
5341   TTGCGCTGGA GCAACTCCAA ACGGAGGACC TTGCTAAGGT CTACCATCTC GATAAGGGGC
5401   CCCTTATGCG ACTATACCTC ATCCTGCTTC CGGACTCAAA GTACTCCTGT CTGTTCAGCT
5461   GCCACCATGC CATTCTCGAT GGGTGGAGTC TGCCCCTGCT CTTCAACAAT GTCCACCAGG
5521   CCTACCTCGA TCTCGTCGAA GGCACTGCTT CGCCCGTCGA GCAGGACGCT ACCTACCTAC
5581   TCGGCCAGCA GTACCTGCAG AGCCACAGGG ACGACCATCT CGACTTCTGG GCCGAGCAGA
5641   TCGGCAGGAT CGAAGAGCGC TGCGACATGA ATGCGCTGCT GAATGAGGCC AGCCGATACA
5701   AGGTGCCCCT GGCCGACTAT GACCAAGTCC GCGAGCAGAG GCAGCAGACC ATCAGTCTGC
5761   CCTGGAACAA CTCCATGGAC GCTGGTGTGC GGGAAGAACT CTCCAGTCGT GGCATCACCC
5821   TTCATTCCAT TCTACAGACG GTCTGGCACC TGGTCCTCCA CTCTTATGGA GGAGGCACCC
5881   ACACGATCAC CGGCACCACC ATCTCCGGCC GTCACCTGCC CGTCCCCGGA ATTGAGCGCT
5941   CTGTTGGTCT CTTCATCAAC ACACTCCCTA TGATCTTTGA TCACACCGTC TGCCAGGATA
6001   TGACAGCGCT CGAGGCCATT GAGCATGTCC AAGGCCAAGT CAACGCCATG AACTCCCGGG
6061   GCAACGTCGA GCTCGGACGC ATGAGCAAGA ACGACCTCAA GCACGGGCTC TTCGACACCC
6121   TCTTCGTCCT CGAGAACTAC CCAAACCTCG ACACGGAGCA GCGGGAGAAG CACGAGGAGA
6181   AGCTCAAGTT CACCATCAAG GGTGGCACGG AGAAGCTCAG TTACCCGCTG CCGTGATTG
6241   CCCAAGAGGA CGGCGACAGC GGATGCTCGT TTACGCTCTG CTATGCGGGC GAGCTCTTCA
6301   CGGATGAGTC CATCCAGGCG CTCCTGGACA CTGTCCGGGA CACCCTGAGT GATATTCTCG
6361   GGAACATCCA TGCCCCTATC CGCAACATGG AGTACCTCTC CTCGAACCAG ACGGCGCAGC
6421   TCGACAAGTG GAATGCCACC GCCTTCCAGT ACCCCAACAC CACACTGCAC GCCATGTTCG
6481   AGTCCGAGGC GCAGCAGAAG CCGGACAAGG TGGCCGTGGT GTACGAGGAT ATCAGGCTGA
6541   CCTACCGCGA GCTCAACAGC CGTGCCAATG CCCTGGCGTT CTACCTCCTC TCCCAGGCGG
6601   CTATCCAACC GAACAAGCTG GTCGGGCTGA TCATGGACAA GAGCGAGCAC ATGATCACGA
6661   GCATCCTCGC GGTCTGGAAA ACGGGTGGAG CCTACGTCCC GATCGACCCT CGATACCCTG
6721   ACCAGCGTAT CCAGTATATC CTGGAGGATA CGGCGGCTCT CGCAGTCATC ACGGACAGTC
6781   CTCATATTGA CCGTCTGCGC AGCATCACCA CAAACCGCCT TCCTGTTATC CAGTCGGACT
6841   TTGCTCTCCA ACTCCGCCCC AGCCCAGTTC ATCCCGTCTC AAACTGCAAG CCAAGCGACC
```

Figure 5 (SEQ ID NO 5) - Continued

```
6901    TCGCCTACAT CATGTACACA TCCGGCACCA CTGGCAACCC CAAGGGTGTC ATGGTGTAGC
6961    ACCACGGTGT AGTGAATCTG TGCGTTTCAC TCTGCCGGCT CTTCGGCCTT CGGAACACAG
7021    ATGACGAGGT CATCCTCTCG TTCTCGAACT ACGTCTTCGA CCACTTTGTC GAGCAGATGA
7081    CGGATGCCCT TCTCAACGGT CAGACTCTTG TGGTCCTCAA CGACGAGATG CGTGGCGACA
7141    AGGAGAGGCT TTACAGATAC ATCGAGACCA ACCGCGTCAC GTACCTCTCG GGGACACCTT
7201    CCGTCATCTC CATGTACGAG TTCGACCGGT TCCGCGACCA CCTGCGGCGC GTGGATTGCG
7261    TCGGCGAGGC CTTCAGCGAG CCGGTATTCG ACAAGATCCG CGAGACGTTC CCGGGTCTCA
7321    TCATCAACGG TTATGGCCCG ACTGAGGTGT CTATCACTAC CCACAAGCGC CCCTACCCGT
7381    TCCCGGAGCG CCGCACAGAC AAGAGCATCG GTTGCCAGCT GGACAACAGC ACGAGCTACG
7441    TCCTCAACGA TGACATGAAG CGCGTGCCCA TCGGGCCGT GGGAGAGCTG TACCTTGGTG
7501    GCGATGGCGT CGCTCGCGGA TACCACAACC GGCCAGACCT GACGGCTGAC CGGTTCCCTG
7561    CCAACCCCTT CCAGACGGAG CAGGAGAGAC TTGAGGGCCG AAATGCGCGT CTGTATAAGA
7621    CTGGTGACTT GGTTCGCTGG ATCCACAATG CAAACGGCGA TGGTGAGATC GAGTACCTCG
7681    GCCGCAACGA CTTCCAGGTC AAGATTCGAG CCAGAGAAT CGAGCTGGGA GAGATCGAGG
7741    CCGTGCTTTC ATCCTATCCG GGCATCAAAC AATCCGTCGT CCTGGCCAAG GACCGCAAGA
7801    ATGACGGGCA GAAGTACCTC GTCGGCTACT TCGTCTCCTC AGCAGGGTCC CTGTCCGCCC
7861    AGGCCATCCG CCGCTTCATG CTCACGAGCC TGCCCGATTA CATGGTTCCT GCGCAGCTGG
7921    TGCCCATCGC CAAGTTCCCC GTCACCGTGA GCGGGAAGCT CGATGCCAAG GCCTTGCCCG
7981    TGCCAGACGA TACAGTCGAG GATGACATTG TGCCACCGCG TACCGAGGTT GAGCGCATCC
8041    TAGCTGGGAT CTGGTCTGAG CTGTTGGAGA TACCGGTCGA CAGGATCAGC ATCTACAGTG
8101    ACTTCTTCAG TCTGGGCGGC GACAGTCTCA AGAGTACCAA GCTGTCCTTT GCTGCCACGC
8161    GGGCTCTCGG TGTGGCCGTC AGTGTCCGCA ACTTGTTCAG CCATCCGACT ATCGAAGCCT
8221    TGTCTCAGTG GATTATCAGG GGTTCGAACG AGGTCAAGGA TGTGGCTGTG GTGAAGGGCG
8281    GTGCCAGTCT TGATATCCCC CTATCCCCTG CCCAGGAAAG ACTCATGTTC ATCCACAGT
8341    TCGGCCATAG CGGCGAGGAT ACTGGTGCTT ACAATGTGCC TTTGCAGCTG CAGCTTCACC
8401    ATGATGTCTG TCTCGAGTCG CTTGAGAAGG CTCTGCGGGA TGTCGTCTCG AGACACGAGG
8461    CTCTCCGGAC CTTGATCACC AGGACCCAGA AGTCCTCCGT GCACTGCCAG AAGATCCTCG
8521    ACGCCGAAGA AGCGCAAAAG CTCTTCTCTG TTGATGTTCT GCGCCTGACC TCGGAGACGG
8581    AGATGCAGGG CAGGATGGCC GAGAGTACCG CCCACGCCTT CAAGCTCGAC GAGGAACTCC
8641    CGATTCATGT ACGCCTGTAC CAGGTTGTAC GTGATGGCCG CACGCTCAGC TTTGCCAGCA
8701    TCGTCTGCCA CCATCTGGCG TTTGACGCGT GGTCATGGGA TGTGTTCCAG AGGGACTTGG
8761    ACGCCTTCTA TGCCGTCCAT ACGAAGCACA AGGCTGCCGC CAACCTGCCA ACCCTCCGCG
8821    TGCAATATAA GGAGTATGCG ATAGAGCACC GCCGGGCTCT CCGCGCTGAG CAACACCGTG
8881    TTCTCGCGGA CTACTGGCTG CGCAAGCTCA GTGACATGGA GGCGTCTTAT CTGGTCCCCG
8941    ATCGCCCTCG ACCGGCGCAG TTTGACTATA CCGGGAACGA TCTCCAGTTC TCAACTACTC
9001    CCGAGACCAG CGCGCAGTTG AAGGAGCTGG CCAAGCGCGA GGGTTCAAGC CTCTACACCG
9061    TTGTGGCGGC GGCGTACTTT CTGCTTCTCT ACGTGTACAC CAACCAGCGG GATATCACGA
9121    TTGGTATTCC CGTTGCGCAC CGTAACCATC CGGACTTTGA GTCGGTTGTC GGCTTCTTTG
9181    TCAACTTGCT CCCTCTGCGG GTCAACGTGT CTCAGTCGGA CATTCATGGA CTTATCCAGG
9241    CAGTGCAGAA AGAGCTTGTC GATGCCCAGA TCCATCAGGA CTTGCCATTC CAGGAGATCA
9301    CCAAGCTTCT TCATGTGCAG CACGATCCAA GCCGCCATCC CCTTCTCCAG GCCGTGTTCA
```

Figure 5 (SEQ ID NO 5) - Continued

```
9361   ACTGGGAAAA CGTACCCGCC AATGTCCACG AGGAGCAGCT GCTTCAGGAG TACAAGCCGC
9421   CCTCGCCTCT GCCTTCGGCG GCCAAGTTTG ATCTCAACGT CACGGTGAAA GAGAGCGTCA
9481   ATTCGCTCAA CGTCAACTTC AACTATCCTA CCAGCCTCTT CGAGGAGGAG ACCGTTCAGG
9541   GGTTCATGGA AACCTTCCAT CTCCTTCTTC GACAACTGGC CCACAACAAG GCTAGCACAA
9601   GCCTCTCGAA GCTGTCGGTT GAAGATGGAG TGTTGAATCC AGAGCCGACT AACCTTCAGC
9661   CCTCAAGCCG GGACAGCGGA AATTCACTCC ATGGGCTCTT CGAGGACATC GTGGCCTCGA
9721   CCCCGGACCG CATCGCAATT GCTGACGGCA CCAGGAGTCT CTCGTACTCC GAACTCAACG
9781   AGCGGGCAAA CCAGCTGGTA CATTTGATCA TCTCTTCTGC CAGTATTGTA GCAGACGACC
9841   GCATCGCTCT TCTTTTGGAC AAGAGCATCG ATATGGTGAT TGCTCTCCTG GCAGTTTGGA
9901   AGGCCGGTGC CGCATATGTG CCCCTTGACC CGACATATCC GTCGCAGAGG ACTGAGCTCA
9961   TCTTGGAGGA ATCTAGTGCC AGGACGCTCA TCACCACTAG AAAGCACACG CCGAGGGGAG
10021  GAACAGTCGC AAATGTTCCA TCCGTGGTCC TTGACAGCCC CGAGACCCTA GCCTGCCTCA
10081  ACCAGCAGTC AAAGGAAAAC CCGACAACGT CAACGCAGAA ACCGTCCGAC CTCGCATATG
10141  TCATCTTCAC CTCGGGAACC ACAGGCAAGC CAAGGGGGT TCTGGTGGAG CACCAGAGCG
10201  TAGTCCAGCT GCGCAATTCC CTCATCGAGC GATACTTCGG CGAGACCAAC GGGTCTCACG
10261  CCGTGCTCTT CCTGTCCAAC TACGTCTTCG ACTTCTCTCT TGAACAGCTC TGTCTCTCAG
10321  TCTTGGGTGG AAACAAGCTC ATCATTCCAC CAGAGGAGGG TCTCACGCAC GAGGCATTCT
10381  ACGACATCGG CCGCAGGGAG AAGCTATCCT ATCTCAGCGG GACGCCCTCG GTGCTGCAGC
10441  AGATTGAGCT CTCCCGTCTG CCGCATCTTC ACATGGTCAC CGCTGCGGGC GAGGAGTTCC
10501  ACGCTAGTCA GTTTGAGAAG ATGCGCTCCC AGTTCGCGGG CCAGATCAAC AACGCCTATG
10561  GTATCACTGA GACGACCGTG TACAACATCA TCACCACGTT CAAGGGCGAT GCCCCCTTTA
10621  CCAAGGCACT CTGCCACGGG ATCCCCGGAA GTCACGTCTA CGTCCTGAAC GACCGACTTC
10681  AGCGTGTTCC TTTCAACGCT GTTGGCGAGC TCTACTTGGG CGGTGACTGC CTTGCTCGCG
10741  GGTACCTCAA CCAGGATGCC CTGACCAACG AGCGATTCAT CCCCAACCCT TTCTACGAGC
10801  CGAAACAGGC AAGTGACAGT CGTCCCCAGA GACTCTACAA GACTGGAGAT CTGGTGCGCT
10861  TCCGTGGACC CCACCATCTC GAGTATCTCG GCCGCAAGGA CCAGCAGGTC AAGCTGAGGG
10921  GCTTCCGCAT CGAGCTCTCC GAGGTGCGGG ATGCCGTCCT AGCCATCTCT GCTGTTAAGG
10981  AGGCTGCCGT CATCCCCAAG TATGACGAGG ATGGCTCCGA TTCACGAAGG GTCAGCGCCA
11041  TCGTCTGCTA CTACACGCTC AACGCCGGAA CTGTGTGCGA AGCATCGAGT ATCCGTGACC
11101  ACCTGCACGC CAACCTTCCC CCGTACATGG TCCCAAGTCA GATCCACCAG TTGGAGGGAT
11161  CTCTCCCCGT GACCGTCAAT GGGAAGCTCG ACCTGAACAG GCTCTCCACA ACTCAAGTCT
11221  CGCAGCCAGA GCTTTACACC GCTCCACGAA ATTCGACAGA GGAAACCTTG TGCCAGCTTT
11281  GGGCATCTCT CCTAGGCGTC GACCACTGCG GCATTGACGA CGACCTGTTT GCCCGAGGCG
11341  GCGACAGCAT CTCCTCTCTC GACTAGTGG GTGACATCTA CCGCGCGCTA GGACGCAAGG
11401  TCACCGTCAA GGACATCTAC CTCCACCGCA GCGTCCGAGC CCTAAGCGAA AATGTCCTGA
11461  CCGACCAGAA GGATAAGGGT ACTCTGCCAG CGTCTCCTCC CCTCCAGCGA GCGGAGCAGG
11521  GCCAGGTTGA GGGCGACGCA CCGCTTCTCC CCATCCAGGA CTGGTTCCTT TCCAAGCCCC
11581  TGGATAACCC CGCTTACTGG AACCACTGCT TCACCATTCG AACCGGGCA CTCTCCGTCG
11641  AAGGGCTCCG GGGTGCTCTG AAGCTGCTGC AGGAGCGCCA GCACGTGCTG CGTCTGAGAC
11701  TGCAACGCCG GGACGAAGGT CGCCATGTTC AGACCTTTGC GCGTGACTGC GCGCAACCTC
11761  GCTTGACTGT GCTAGACCGA CGAAGCTTCG AGGACGCAGA GGATGTACAG GAGGCTCTCT
```

Figure 5 (SEQ ID NO 5) - Continued

```
11821   GCGAGATCCA ATCTCATTTC GACCTCGAGA ATGGACCCCT CTACACAGTG GCGTACATCC
11881   ACGGTTACGA GGACGGCTCC GCCCGAGTGT GGTTTGCCTG CCATCACGTC ATGGTCGACA
11941   CTGTGAGCTG GAACATTATA CTGCAAGACC TGCAGGCTCT CTATCATGGA GACAGCCTTG
12001   GTCCCAAGAG CAGCAGCGTG CAGCAGTGGT CGCTAGCTGT CAGCGACTAC AAAATGCCAC
12061   TGTCGGAGAC GGCGCATTGG AATGTGCTCA GGAAGACAGT CGCCCAGAGC TTCGAGACCC
12121   TGCCTATCTG CATGGGCGGC GTGCTCCAGT GCCAGGAGAA GTTCTCGAGG GAAACGACAA
12181   CAGCTCTGCT CTCCAAGGCC TGCCCTGCCT TGGACTCCGG TATGCATGAG ATCCTTCTCA
12241   TGGCCGTGGG CTCCGCGCTG CAGAAGGCGG CAGGGGATGT CCCTCAGGTC GTCACGATAG
12301   AGGGTCACGG GCGCGAAGAT ACTATCGACG CAACTCTGGA CGTCAGCCGG ACAGTCGGCT
12361   GGTTCACGAG CATGTACCCC TTCGAGATCC CCAAAGTGAC CGACCCCGCT CAGGGCGTCG
12421   TCGATGTCAA GGAGGCGATG CGTCGCGTGC CGAATAGGGG TGTCGGTTAC GGTCCAGCCT
12481   ACGGATACGG CGGATCGTCG CTGCCCGCGG TGAGCTTCAA CTACCTTGGT CGCCTGGACC
12541   AGGCTTCCTC GGGGGCTCAA AGGGACTGGA CGCTGGTCAT GGATGAAGAC GAGTATCCGG
12601   TCGGACTGTG CACCAGCGCT GAGGACTCGG GACGAAGCTC CTCCATGGTG GATTTCACCT
12661   TCTCTATCTC TGGCGGCCAG CTTGTCATGG ATATGAGTAG CAGCTGGGGC CACGGCGCAG
12721   CAAATGAATT CGTTCGCACA GTTCGTAACA CACTAGATGA CTTGATCAAA CAACGAGCA
12781   GCAGGGACTT CAGCGCACCT CTGCCTCCGT CGGATCAGGA GTCCAGCTTC ACCCCTTATT
12841   TTGTCTTCGA AGAGGGCGAG CGACACGGCG CTCCGCTCTT CCTGCTCCCA CCTGGCGAAG
12901   GCGGAGCGGA GAGCTACTTC CACAACATTG TCAAGGGTCT CCCGAACCGC AATCTTGTCG
12961   TGTTCAACAA TCATTACCGC GAGGAGAAGA CGCTCCGGAC CATCGAGGCG CTGGCCGAGT
13021   ACTACCTGTC GCACATCCGA TCCATCCAGC GGAGGGGCC ATACCACATC CTCGGCTGGA
13081   GTTTCGGAGG CATCCTCGGT CTCGAGGCGG CAAAGCGATT GACTGGCGAG GGTCACAAGA
13141   TTGCCACGCT GGCACTTATC GATCCGTACT TTGACATCCC GTCCGCGTCC AAGGCCATCG
13201   GCCAACCTGA CGATGCCTGC GTCTTGGACC CCATATACCA CGTCTACCAC CCGTCGCCGG
13261   AGAGCTTCAG GACGGTGTCA TCTCTCACTA ATCACATAGC CCTGTTCAAG GCTACCGAGA
13321   CGAATGACCA GCATGGCAAT GCCACGCAGC AGGCCCTGTA TGAGTGGTTT GCCACGTGCC
13381   CTTTGAACAA CCTGGACAAG TTTTTGGCGG CCGACACGAT CAAGGTGGTT CCTCTGGAGG
13441   GTACACATTT TACCTGGGTG CACCACCCGG AGCAGGTGCG CTCAATGTGC ACTATGCTGG
13501   ATGAATGGCT TGGGTGAACG AGGCAGTTGC TGTGAGAGAA TGAGAATGAG ACACAAAACG
13561   CGGGCGGAAG AGAGACTTCC TCGGACGGCG GGTTTCCGCC GACGAGTGAT GACCTGGTCC
13621   CAGGGGTCTG GTGATATTTT CTCCTGAATG TGTGAGGATA TTAGTGGTTT TTTTCTGCCG
13681   TTAGAGACGT ATTTAGTAAG CTCTGGAGTT TGGAGTCATT ATTTTCCTGA ATGGTCTTCT
13741   TCTGTAGTAA TAAACTAGCA GAGCGGATTA TATATATATA TATATATATG TATTTGGCTG
13801   GTATTGCTAT GCGTGTTCCT ATGTGAATTG GTATATGTAT AAGTATGTCT ACCTTACTGC
13861   ATCTGTTAAT TCTTATGTAC TGCTACATGA GTTGCTACGG TTATTGCGAC GTGATGCGTG
13921   TAGTCGAAGT TATTGTACCT ATTGCGTGTA CTATGCTCCC CTCTTCTTTC TACTATATCT
13981   CGGTGTAGTA CAAACAAAAC GACGTAGGGG AAGTGGGGAA GAAGTTGAAC GAGTATAGAC
14041   TCCCCGAGCA ATGAATCAGT ACATTATATA TACTGTTTCT TCTCTCTCAT GACTTGGTAC
14101   GTGGGAAGTT CCCAACATCT AACCTGTCCA ACCCTCCGAC CAGAAAGCTG TCCAACAATG
14161   TCGTCCAACG CTCCCAGCTC CCCAAGTATC ATCCATGGCA CCGAAGGAGC CGCATCATCA
14221   ACTGAAAGGC ATCATCTTTG GACTATCGCA CCGGGATAAT TCTATACGAC ATCCAAGTTG
```

Figure 5 (SEQ ID NO 5) - Continued

```
14281    AATTGTCTGA GCCTCAGGTC AGGATCCCAG GCGTCAATCT TGGCAGGGGA TAGTGAAACC
14341    TTGAAACAAG GCATGCGGGC ATTGCGGGCA TTAGGCTCGC ATAGAGAGGG GGGGTTCCAG
14401    ACCGAGAGAT ATGCGTGCAG GGCCACGATA TTGGTGCGCC CAATTACTAG CATAAAATAC
14461    TAATACAAAT GCAGGCAACC GAAGGGGATT ATTCATAAAT GCCTTGGGTG CATGGCAACT
14521    CGAAAAGTTG GGGAATGTGG CAGGAGCGCC CAAGCATATT CACTCGTCAA GAGTCGTCAT
14581    CACCACCCCC GCCCACCTTC CTATCTTATT CCTCCTCCT TCAGATCGTA CGACACTCAT
14641    CTTCCCTCGT CTCTTTTCCA TCGTCGTCAT CAACAAAAGT CATCTGGCTC GTCTCCATCC
14701    GAAACACCTA CTAGTAGCTA TTAGTCACTC ACTATGAGAC TCTCCTTCTT CGCGCCAAAC
14761    CGTACGATAA AAAGTCCTTT GGCCTCGCCC ACGCCGCCAG GGATCCGCCG TCACCCGTCA
14821    CGATAACCTA CCACGACATC CCCCTCAATG AGGACACCGT CTCCACGGTT AGGGACGCCG
14881    ATGCCGTCTG CGCCTTCGTA AATGACTCCC TCTCCGCTCA CGTCATCGAG ACCCTCGCCA
14941    GGCAGGGTGT CAAGGCCATC CTCCTCCGCT GCGCCGGCTT CAATCACGTC GACCTCGCCG
15001    CCGCCGCCCG ACACGGCATC ATGGTCGCCA ACGTGCCGTC GTACTCGCCA GAGGCCGTCG
15061    CCGAGTTCGC GGTAGCCCTG ATCCAGACAC TCAACCGCAA CACCCACCGC GCCTACAACC
15121    GCGTGCGCGA GGGCAACTTT GCCCTCCACG GCCTCCTGGG TAAGACACTG CACGGCAAGA
15181    CGGTCGGGCT AGTGGGCGTG GGCAAGATCG GCTTGGCCAC GGCGAGGATC ATGAAGGGCT
15241    TCGGGTGCCG CGTCCTTGCT AGCGACCCAT TTCCCTCGCC TGCGTTTGAG GAGTACGGCG
15301    AGTACAAGGA CCTGGACACG TTGCTGTCCG AGTCGGATAT TGTCAGCCTC CACTGTCCCC
15361    TCATGGACAA CACGCGGCAC ATCATCAACG GCGACACAAT CGCCAAGATG AAAAAGGGTG
15421    TCCTCCTCAT CAACACGTCC CGCGGTGGCC TTGTGGACAC CCGTGCAGTC ATCAAGGCCC
15481    TCAAAACAAA GCACATTGGC GGCGTAGCCC TCGACGTGTA CGAGGCCGAA GGCTCACTGT
15541    TCTACGACGA CCACTCCGGT GAGATTATCC ACGACGATGT CCTCATGCGC CTCATGACAT
15601    TCCCCAACGT CATCGTCACG GGACACCAGG CCTTCTTCAC CGAAGAGGCG CTCGAGGAGA
15661    TTGCACAGTG CACGCTGCGT AACCTGGAGG AGTTCATCAA GGAGGGAACA TGCAAGAACT
15721    CGCTGACCAA GGAGCCCGAA TTGAGGTCCA AGGTCCCTGA CCCGGTGCGC AATGTTTAAA
15781    TTGATGTGGA TGATTGAATT CTATATTCTG GTATCTCTGT CTATGTACGG TCATCTGAAA
15841    CTTTTGATGC TGGTTAAATG GTGAGTCCTG CTAACGCCAC ACACAAACAC ACACACGCAC
15901    ACACACAGNG CATATTGAGA CGAAACTGGG GAAAGCTAAG TATCAATAAA ACACAAAACG
15961    AAATGGACGG AAGGATATCT CCCGCTCTAG TATATAAGGC GTACGAAAAC ACCCGTTGTA
16021    CAACCGCTTA AG
```

Figure 6 (SEQ ID NO 6): A. chrysogenum genomic DNA sequence of an approx. 5.8 kb region marked by EcoRV and BamHI and containing the biosynthesis genes cefD1 (position 2372 to position 180, inverse arrangement) and cefD2 (position 3888 to position 5133). A single strand in 5'-to-3' orientation is shown. The particular translation start codons (ATG) and the particular translation stop codons (TAG) of the respective coding regions are depicted underlined and in bold type. The intron cefD2 and the said cleavage sites are depicted underlined.

```
1     GATATCTGAG TGGTTGTTCC GCGCGTTACG GAGTCATAGC CGGTTGAGTT CGGCCGAATC
61    TGCCCTCTAT GTTGTGTTTA CGCTCTTCAG GCTTTATGCG GAATTACATG TGTTTTGCAA
121   GCCACATTTG TTTTCTATGT TACATCGTTT CACGCGTCGA TGGGTCCCGT TAATAGCAAC
181   TAGAGTCTTG GCCGAGCCGC CGACTGGCCG GACAGTAGAT CCCAGTCCCG CTCGGTAAAG
241   GGAACATACT TGCTCGCACC GGCCGGCAGC CAGAAGAAGC GATCCTTTTC ACTTCCAGGG
301   ACCTTGCTGC CCATGGAGCG CGGGTCGACC CCCTCGTCGC GGAGTGGCAC CTTGTTGTGT
361   TTATGGTTAT CCGTGCTCAT GCCTCCCACC GTCTCCCGCA CCCTAATGAA GACAGGAACG
421   GCGTAGGAGG GCAACTCTGA CCGCAGGAGC GACGTCAGCC GTGACCAGTC CAACGTGTCT
481   GGGGTTGCCG CGTTCTTCAA TGCGATGGCT GCGCAGCCGG CTCGCCCGTC GTGGTTGGGG
541   ACCTGGACGC CGTAGACATT GGCCTCGGCA ATGTCTGCGT GTGAGCCCAG GACTTGTCCT
601   ACCTCGGTCG TGGACACGTT TTCTCCTTTC CAGCGGTATG TGTCGCCTGG TATTCACGTT
661   TAGCATTGTC ACTCTGCGAT TGTAGCAGGG ATAACGTACC AAGTCGGTCG AGAAAGTACC
721   AGTGACCGTC GGCATCGCGT CGAAGTACCA GTGACCGTCG GCATCGCGTC GAAGAGCATC
781   ACCCGTCCGG AAGTACAGAT CCCCCTTCTC AAACACATTC TCCACCAGCT TCTTCTGCGT
841   CGCCTCCTCA GCATGCCAGT ACCCAGCCCA GGCTGACCGT GACGGGAGCC GCGCCAGGAT
901   CTCACCGCCC CTCTCGTACG GCAGTCGCTC GGCAAAGCCC GTCTTCGGCG ACCGCCAGAT
961   GTCACCCGTC TCCGGGTCGA TCCTGACGGG TACGTAGTCA TTGTGAAACT TGCGGCGGAG
1021  GAGCCAACCG TGGTGGCCGA CGGCGCCGAG GCCGAAACCA CCGCCGCGGT AGTGTTTTAA
1081  GAGTGTCAGG ACGCCTTCTG TGCTGGCGTA GAATTCACCG ATGTCCGATA CGCCGAAGCG
1141  GTCCTGTTTG TCGCTTGGTG TCAATCCTAT GGTTTCGATG GGGCTGGACC GAAGTAAAGG
1201  GGGATCATAC CTGGAATTTG GTCCAGAGTT CCGGGCTGAG TCCGTTCCCC CAGACGAGAC
1261  GGACGCGGTG CTGACGGTCC TTTGGTGAGG CCGGAGCAGA GAGTAGGTAC CGAATAAGTT
1321  CCCCGACTGT ACACTCGTCA GGAGGGCAAA CAAGTCGAAG AAGGGTACCA AGGGAGAGTA
1381  GTGGCTTACC ATAGACAAAT ATTGTTGACC CGCTCTCTAT GCAATCGTCC CAGAAGCGAG
1441  ACAAGGAGAA CTTGGGCGCA AGAGCAATGG ATATTCCGCT CATCAAGTCG TTCATGGCCG
1501  CGATGCCCCC CGTTCCGTGG TAGAGCGGGA TGCAGTAGTA GGTGCGGTCA CCGTTGGGGC
1561  CCGGTTTCTG CCCAAATGTC TTTGGCAGCA GTGAAGCAGA GGGATAGTTC CTGGCCACTG
1621  TGATGGGTGC GGCCTTTGGC AGGCCAGTCG TACCACTTTT GCCGTGAGAA TGTGCAACTG
1681  GTGGGTGAAG TCCGAGGCTT TACTCACCTA GTGTACATCA AAGCAAACGG TAGCAGCACC
1741  TTGGTGTCCT CGAAGCAATC TACCGGTGCC CTGTGTGTTT CTTTCCGGGC AATGTCTTCC
1801  TTCAGCGTGC CGGAGAGCAT GATAGCCTCG ACATTGATAT CCCGAAGCCG CTCACCAACT
```

Figure 6 (SEQ ID NO 6) - Continued

```
1861    TCGTGAATGC GAGAGGAACA ATCGGACGCA TCATCGTATA TCAGAAACCG CGAGCGCGAC
1921    AAGCGGACAC AGTGAACCAG AGCATCAGAG CCGAGATTGT AATTGATGAG GGCAGGAGCA
1981    GCACCGATAG ACAGTAGACC CATCCAGATG AACATCAGCT CCGGCGAGTT GTACAGATAA
2041    ACACCGACGT GCTGCCCGGC CACCACGCCC AGATCGCGGA AGTAGTGGCC ATACTGACAT
2101    GCGCGTTGGT ACGTCTGCGT CCACGAGTAC TCGGGGTGCC CGCGCGACCA GATGCAAGGT
2161    GCATCGCCGA GGCGGGCAGC GGCGGCCTCG AAGAGGAAGA AGCCAGATGC CTTGCGCTGC
2221    TCAACAGCTC TGGCGAAGTT CTGGGCCCCC CGTTCGGCGC GGGCGAGCTG GTTGAGGTCC
2281    TTGGTGAGGT GAAGCTTGGC GTCGAGGTAG GCAGCGGCGG CGGTGCTGGC GGCAGCGGCG
2341    CCAGCGAGGG TTAGTAGGCC GCCGGCTGCC ATTGGGGATT GCCGTTATGC TCCCGTGTGT
2401    GCTTGTGTCT TTGCGAGCGA TGTCCTTGCC TCCGAGACAT TGGTGCTGGT GCTGGTGGCT
2461    TTGACTGTCT CGGAGAAGGG TGTAAGTGAT CGTGCGATCG GGAGTCCAAA AGTTGACCAA
2521    ACACGGACAC AACCAGTATT GACGAATAGT TGTTGAAGAC TGCTAGCCTC GGCACCCAGA
2581    AGCTTGGGAG ACCTGATGGT GTGGCGGGTC TGTGGGTTTG GCCCTTTTG  GGAGGGGGCC
2641    AAGGGACATG GATGGAGGGA GATCGGCGGC GATGTTGCGG CCGCACTAAC AAGAGGTGTC
2701    CGTACGTCCG GACTCCGTAC GGTACTGTAC GGCGCCCGTG GAACCAGGCA CTGAAGATTC
2761    AAGGACTGTT CCTGTCGGAT ATGGCCGCGG CCATGCGTGT CCAGGTTATA GTCTCGACTA
2821    CATACAAACA TTGTACCTTA CGTAAAAGAA CATGGACAGT AATACGCTGA CTCTTGGCTA
2881    CGGGATGATA TTCACTGCCC AAGACCGACG CCAAGCAGCG CATACTGTAC GCATAGGCTA
2941    CGTGGTGGAA ACACCGTGGC CAACTCATCC CTTCGTACGG TACAACAGCC GGACAGGGGG
3001    TGAGGGCGGG TCGGCTCCGC GGGCAGAAGT GCTTACAGCT TAAGAGCTAG TGGTTAAGGT
3061    TACATGTACT AAGCATTGGT CTGGATCGAA TCAGATGCTG TGCCTTGACT GGATCGAGCG
3121    GGCCGGCCCC CTGCGTCTTA ATATAGCAAG TACCCGTGAC TATGTAAGTT GTACATGTAC
3181    ATCTGTGCTG CCACAGGAGC GCCTATAATG TACACCCACC TTGCACGAAC ATTACATTGA
3241    TACTTGCGTT CTCCGTACA  TGACAGGGGG GTGATATTAC AGTACATGCT CCGCCAAGTA
3301    ATACAAGACA CGGACCATCG GAGGCAAACA TTTGTACTGC AGAATGATGC CTGATTTAGG
3361    CGCACAGTCT GCATACATGC CATGCCATAA TGAGGTCGTG TATCCGTAGT CTGTGCTCTG
3421    GATGACTATG AATTATGTCT GAAGTTATTA CTTGGCAACA ACCTGCTTGC CCAACTGGGC
3481    AGGTTTCATT CATGATGGGA GGATGGAGAC GATGAGTCTA TCCTTGGACA CTGGCATGCG
3541    CCCCGTCCTT GGTGCAGCTA GATTTTCAGC TTCGATGCAC AGGCTCCGCC CTTGATACTA
3601    CAGCAGAGTA CATGCCGAGA CAAGAATCTT CAACGTCCCC GATGCGCTTT TGATATCCAC
3661    CCATGTTTTC ATAGTCGCTG CGCGGTATCG GACCCGAGTC GTCTGTACAC GTGGGTAGAA
3721    GTTACGCGAA TGCCACCTCA CCACGCTGCA CCATCCATGC CGAGGCAGGC TTCGAGATTG
3781    CAAGTACGGA CTACAATAAC ATCAAATGGC ATGGTGGGAT TTCCGCTGAC CACCTGCCGA
3841    CATTACATGT TGTAGTCTTG ACCATTCACG CGGTTAATCC CACCTCGATG GACCCCTCTC
3901    GCCCACATCC GCTATCCGGC AAGCTTGTCG TAGAGCTCGC GGGGCTAGCC CCAGGTCCGT
3961    CATCCATAGC CACTTTCATG TTGCTCTGCC GAGAGGCCTA CGCATAGAAG CCGCTTCTTG
4021    CGCTCACGCA CTAACTCGCG CACTCCAGGC CCATTCTGTG GCATGCTCTT GGCAGACTAT
4081    GGCGCCTCAG TACTCCGCAT CGACGGACCG CGATCCCAA  AGGGGGACGT CCTGGCGAGG
4141    AACAAGTCGT CCATCTGCAT CGACTTGAAG CATCCGCCCT CACGCAAGGT GCTCCTCTCC
4201    ATCCTGTCCC GCGCGGACGT GCTCATCGAC CCGTTCCGGC CCGGCGTCCT GGAGCGTCTG
4261    GGGCTCTCCC CCACAGAGGT CCTTCTCAAG GCGAATGCCC GCCTGGTGGT CGCCCGTCTC
```

Figure 6 (SEQ ID NO 6) - Continued

```
4321    ACCGGCTTCC GCCGAGATGG CAAGTACCAG GACATGGCAG GCCATGATAT CAACTACCTC
4381    GCCGTGTCTG GCGTCCTGGC TATGCTTGGT AGGGCAGGCG AGAATCCCTT CCCGCCGGCC
4441    AACATCCTCG GCGACTTTGC CGGAGGGGGC GCCATGTGCG TCGTGGGAAT TCTGCTGGCG
4501    CTCGTATCGC GCGATGCCAC GGGGCTTGGC CAGGTCGTCG AGGCCAACAT GGTGGACGGG
4561    TCTGCGTACC TGGCCACGAT GCCGCGCCTG GCGACCAAGA CGCCCTTCTG GGGTTCCCCG
4621    CGGGGCGAGA ATGTCCTGGA CGGAGGGTGC CCCTGGTATG CGACATACCG GACAAAGGAC
4681    CCCGGCGGGA AGTACATGGC CGTGGGAGCG CTGGAGCCTC ACTTCTACGA GGTGCTGGTG
4741    CGAGGTCTGG GCCTGGACAA GACGGACCTG CCTCCGCGGG AGGATAGGGC CAATTGGCCG
4801    AGACTGAGGG CGCTATTCGA GGCAAAATTT GCGGAGAGGA CGCGCAGCGA GTGGGCGGAG
4861    GTCTTTGACG GGACGGATGC CTGCGTCACC CCGGTCCTGG AGCAAGGTGA GCTGGAGAAG
4921    GCCGGCTTCG AACAACGGCT TCCCGTGAAT TTGGGGGCCA CGCCGGGAAA GCCTATTCTT
4981    CCCGGACAGG GTGATTGGAC GGGGCGGACC CTTGCCAAGG GCCATGGAGG AGAGGAGATC
5041    CTGCGCCGGT GGATTGGGTG GGAAAGGGGG GTTGACTACC ACGTTGAGGA GAATAGCGGA
5101    ATTCTCGTCG CTTGTTCGCG GGAAAAGTTG TAGGCAGGCA GGCAGGCCAT GCTGGTACAT
5161    GCATGCAATG TTGGCCGCTT ATGTACGTAT GTGCATACAT AAACATTGAC AATAGTGGTG
5221    TCATGAAGGA GGAGGGGGGG GGTGGGTTTC GGCCCCTGAC GGTGGCTTGA TCGGGACATG
5281    GACGCCGCAT CGTCAGCGGA GTCAAGCCTC CCGACAGACC TGCCGACCCG ACATCCGAGT
5341    ATCTGTACGT AAGATTGCAT ACCAACAATG TACACCTACT TCCTACGGTT CCAGGATTTT
5401    CTCTCTGGAG GTTGCATGGA GCGAAATGAA AAAAGAAATG CTGCTGCCTG TGTTGGAATT
5461    CACAGCCTTG GGATGCGACC TCCCTTTTCA CCGTCTTCAT CCTCGTTGGG GACTCTCAAC
5521    CATGCTGCTG TCGCACTCAG ATAATACAAG GCGTAATTAC TGCAGCGGTA CGTCGTAATT
5581    GGACTTACTT TTGTACGACA GTTGATGTCC AGCGGCATAA AAAGCCTCAG CCGCCAAGAC
5641    TGGCAGACTT CTGCAGCCCT ATCTTGATAT GATCACCCCA TAGGCCGAGG CCCTGTGCTC
5701    GAATCCCGCA CGAAGCCGGA TTCATGTGTA TTCCCAAGGG GGTGAGGACG GAACTCTTAT
5761    TTCGACCTCC GGGGGGCCGA GTTCTAGTCC GCTAACCTTC ACGGCTACAC CGTCCCTCGC
5821    GTCTCAACTA GCCATATAAG TCCTAGGTAA AGAGGTTAAA GTAGGTAGGA AAGGAACTTG
5881    TGGCTTGGCG GATCC
```

Figure 7 (SEQ ID NO 7): A. chrysogenum genomic DNA sequence of an approx. 4.6 kb region marked by XbaI and SgrAI and containing the biosynthesis genes cefEF (position 1118 to position 122, inverse arrangement) and cefG (position 2058 to position 3534). A single strand in 5'-to-3' orientation is shown. The particular translation start codons (ATG) and the particular translation stop codons (TAG, TGA) of the respective coding regions are depicted underlined and in bold type. The two introns in cefG and the said cleavage sites are depicted underlined.

```
1      TCTAGATACC TTGAAACTTG AAACTCTTGA CACTCATGCT TTGTGTTTTA AAAATTTAGC
61     AATTTATAGG GCAATTTTTC TTCTTAAACT CCCGTAGATT TATTACTCGA TCGGCGGTTC
121    CCTAAGTGGC TATAGGAGCT GCGGTAGAGA CAGGGGCAGC CGCGGGGACA GCCGCCTCCG
181    CTGCCGCCGG CTTATCCCTC CGCATGTTGA CATAGTTCCC GCCAAGCCAC TCCCTGAACG
241    TCGTGCGCTC CGACGGGATG CGGACGTTGA AACCCCACTC CCTCGACTGC TGCACGTTGA
301    AGCTGAAGTC GGGCTTCGGC CGCAGGAAGA AGACGCTCGA CGTGCGGCTG CTGCCGACGC
361    GCTGGTCGCG CCCGGGAGAC TTGACCCGGT GCTTGGGCGC CTTGACCTTG CCGCCCGTGG
421    CCAGGGTGCC GACCGCGCCG CAGAAGACGA CCATGGCGCC GGGGAGCGTC GGGAGGTCGA
481    CGAATTCTCC GTCCACCTCG CACTGCAGGC TCACGAAGCC GTTGGCGCAG GCTGTCTGGT
541    GCACGAGCGT GATGGTCGAT AGGTCGTAGT GGGGTCCCAT GCGGAGGGGT TCCTCTTCGG
601    CGACGCGGTC CTCCGGCACT TCGGGGAAGT ACCGTAGGCG GAGGAGGGGA TCGCACTCGA
661    CGAAGTCATC AATGTCCTCC CCGGCGAGCG GGGCGCCCAC AGAGTTGAGA ACGGCGCGCG
721    CGACATCCTT GGCTGCGCCG TACATGCGGT CGAAGTAGTC CTGCCAGACG TCCTCGAAGC
781    CCCGGTTCGG GAACAGGTTG CCGCCGATGC CCATGGAGTA GCACGTCGAG TAGTCCGAGT
841    ACTTGCCCGT CTCGGTGACG ACGGCGGTGC TCTCCCACTC GAGGGCAGAG AAGCCGCGGC
901    GGGCGTTACG GTCGGCGAGC GTCACGGCCC TCTTCTCCTC CTCGCTTCCG TTCTTGAAAA
961    AGTCAACGCA CGTCTCACGC GCCGAGGTGT GGTCGTCGTC GACCAGGCCG CTCTCGGTCA
1021   AGTAGAAGAT ACCCTTGGTG GTGACGGCCT CGGCGAGCTC GGTGAGGACC TTGCCGCTCT
1081   TGAGGTCGTC GAGACGAAAG ACGGGGACCT TGGAAGTCAT GTTGATGCTG TGGTTTTGAG
1141   CGATGACTTG AGAGGAGTAG CGTGGAGGAA AGTTCTGCAA GAGGAATTTA AGGATTCACA
1201   AGATCCCAGT GAGAACGAAA CGTTGTCAAA GCGGTATATA TATATCTCAA ACCCCACCTC
1261   GTAGCTTACG CCGAGGAACT CCTTTTTAGA CAACTGCTAC TTAGCCGTAA GTGACGCCCT
1321   GCTTCCCCTC AGCCTTGGCC GCACACGTCA ATGTAGCATT GTAAACCCAC GAGTGTCTTG
1381   TGAAGTTTTG TCAACGAATC ATAAGAAGCC ATCGAGTTCT CTTCTCGTTC TTGGTTCGCA
1441   GGAGAATATG TATCGTGCAT GGTCCCTGAT CGTCGAGACC GCCATGGAAT CGTGCAAGCC
1501   TTAATTCTCC GTACAAGCTT CCCCATTCGG ACAAGATTGC GATGATGTGG ATGCGGGCTC
1561   TTTTAATAAG GACCTTCTTA ACCGATGGTC CGAGAGTGCC TAGGACGGGT CCATGTGCAT
1621   ACACGACGGA CCCTCGACCT CCTATTAGGA GCATGAGGGA CGACAAAATG CGAACGACGA
1681   TGCATCAAAA TGCACTGCAA CGTCGAGTTG TGGGCTACTC GCCTTCTGAT TCGCAAGCCC
1741   TCGGCGAGTC CACCTACTAG TAGCTTGGGA ATAAACAGCA AGTTTCGCCG CCAAAAGGGC
1801   TGCCCGGCAT CCGATTCGAT GCCATTGTAC ATCAAGTCGG AAATGGTGCT CCGTTTCCCC
```

Figure 7 (SEQ ID NO 7) - Continued

```
1861    CTGGGGTGAG AGGGCGAAGG AGTAGTTCGA CCAGTCGCAG CGCACCCAGA GCCGCAGGTT
1921    TTATCGGATG TTGCTTCGAT CCGATCGTAT CCCGCGCGGC CTAGATCTTG CTAATACGAG
1981    TCGAGAGTT  ACTATTCCGG GCTTATGCGG ACGGGCCGCC GCCGTCGATG CCGGCCAAGG
2041    CTTGTCGTGC ATGATAGATG CTGCCGTCGG CCCAAGTGGC CCGTCTAAAG CCGGACCCCT
2101    TTCCCCCGAG TCTCTCCCCG ATCCCGCACG GGGCCGTCAC TTTCGCTGCC CTCGCTCCTT
2161    GTCATAACCT ACCTATATTC TCATCCCGGC AAATGCTGCG GGATAGCCTC ACCTACAGCC
2221    ACACGTCGCC CACCATGTCG CCTCAGATCG CCAATCGCTT CGAGGCTTCG CTAGATGCCC
2281    AAGACATAGC CAGAATATCG CTCTTCACAC TGGAATCTGG CGTCATCCTT CGCGATGTAC
2341    CCGTGGCATA CAAATCGTGG GGTCGCATGA ATGTCTCAAG GGATAACTGC GTCATCGTCT
2401    GCCACACCTT GACGAGCAGC GCCCATGTCA CCTCGTGGTG GCCCACACTG TTTGGCCAAG
2461    GCAGGGCTTT CGATACCTCT CGCTACTTCA TCATCTGCCT AAATTATCTC GGGAGCCCCT
2521    TTGGGAGTGC TGGACCATGT TCACCGGACC CCGATGCAGA AGGCCAGCGC CGTACGGGG
2581    CCAAGTTTCC TCGCACGACG ATTCGAGATG ATGTTCGGTA GGTAAGCGCA CCGATCCAGC
2641    TTGTCTCAAT ATCGAGTGGT CAGGACAATC CAGGCTAAGC TTTCCGTGTC CAAAAGTATT
2701    CATCGCCAGG TGCTCGACAG GTTAGGCGTC AGGCAAATTG CTGCCGTAGT CGGCGCATCC
2761    ATGGGTGGAA TGCACACTCT GGAATGGGCC TTCTTTGGTC CCGAGTACGT GCGAAAGATT
2821    GTGCCCATCG CGACATCATG CCGTCAGAGC GGCTGGTGCG CAGCTTGGTT CGAGACACAG
2881    AGGCAGTGCA TCTATGATGA CCCCAAGTAC CTGGACGGGG AGTACGACGT AGACGACCAG
2941    CCTGTCCGGG GGCTCGAAAC AGCGCGCAAG ATTGCGAATC TCACGTACAA GAGCAAACCT
3001    GCGATGGACG AGCGCTTCCA TATGGCTCCA GGAGTCCAAG CCGGTGAGTT TATAGATGCC
3061    TTGCCGTCGG TCGATGCTCA GAGCTAATCA GACCGAACCC GCTGCTAGGC CGGAATATCA
3121    GCAGCCAGGA TGCGAAGAAG GAAATCAACG GCACAGACAG CGGCAACAGC CACCGTGCTG
3181    GCCAGCCCAT TGAAGCCGTA TCTTCCTATC TCCGGTACCA GGCCCAGAAG TTTGCCGCGA
3241    GCTTCGACGC CAACTGCTAC ATCGCCATGA CACTCAAGTT CGACACCCAC GACATCAGCA
3301    GAGGCCGGGC AGGATCAATC CCGGAGGCTC TGGCAATGAT TACACAACCA GCGTTGATCA
3361    TTTGCGCCAG GTCAGACGGT CTGTACTCGT TTGACGAGCA CGTTGAGATG GGGCGCAGTA
3421    TCCCAAACAG TCGTCTTTGC GTGGTGGACA CGAATGAGGG TCATGACTTC TTTGTAATGG
3481    AAGCGGACAA GGTTAATGAT GCCGTCAGAG GATTCCTCGA TCAGTCATTA ATGTGAGGCT
3541    ATGGAGGTGT CAGCCTGCCG GTGCGCGTAC TTGCCAGGGT GATCGATGTA CTCTCAGATA
3601    GTCTCCATGT GAGTATGGAT TTCGCTGTTT CCGCTCGGAT ATAGGCACTC TCAGGCCATC
3661    TCGCAGTAGG TATCAGAACA GCAGCTGAGG CCTTCTCGGA AAGTAGGTTG TGTCAATAGA
3721    TTCATAAAGC GTCAAATAAA GCCCAAAGTC GCAGTAGACT CATCGCATCG CAAGTCTCAG
3781    AGGGTCGACT CGGCAGATTC GAGGCATTGT AGCACATTGT CGAGGCATTG AGGCGGAGAC
3841    TTGACCCATC CAACTCGGCC AGAGGCAGCA GGCAAAGCAT CTCAGCGTAG GCTCCATGCA
3901    AAACATGCGT GGCTCAACTC AGCAAGCTCA TTGCCAACGA GGTCAAAGAA AATAGAAGGT
3961    AGCGGAGGCA GGCGGGTATC GTAGTAACAC CGTCCACATA ACACGGGCTC AGCGGAGCAA
4021    CGTAGTACCT ACTCGTATAG AGGCACCGCG TCAGGAGAGG TATCAGAACC CTCATGATTC
4081    TATCGCCATG CTGCTGCGAA CACTAACAAA TGATAAACAA GGGCCCATGC TGTGTGATGA
4141    TGATTCAAGC AGGTTGTCGT GGTCCAGGTT TGGTGCCCGA GCCCGCACA  GCTGAAGATG
4201    ACGCGTCTCG CTGTCGCGCC TTCCACGACC CAGAAGTTGA TGTGCAGAAT GGGCAGTGAG
4261    TGAACCTGGG CGGGAGTGAT GGAAGGTGCC TACCCTGTAC AACCAACTAC GTCGGTACTC
```

Figure 7 (SEQ ID NO 7) - Continued

```
4321    GTAGGAGCAA TAGCGATGAA GCGTCGGGAG AGAAGTGTGA ATTACTCTGG TACCTGGTAC
4381    TTGATGCAAC ATAGCACATT TCACCCATCA AAGCTAGGTC CCGCGGCCTG GGAGTGGAAT
4441    GGTGAAAGAC ACCGAGGCAA ATGCGGCATG AATGAGGAAG CACGGACGAG TCGTGGTTTC
4501    ACAAGAGACA CTCTGACCGA CCACAAGATT CGGCAGTACA GTCACAGCAT CACCATCGGC
4561    AGTCAGACAT GATTCAGAGC CAGGTCTTCG GCAGAGGGAA TTAGATACAC CTCGGCACCG
4621    GCG
```

PROCESS FOR PRODUCTION OF CEPHALOSPORIN C

FIELD OF THE INVENTION

The present invention relates to isolated nucleic acid molecules which code for a new protein from *Acremonium chrysogenum*, to vectors which comprise such a nucleic acid molecule, to *Acremonium chrysogenum* host cells which have been transformed with such a vector and to a method for production of cephalosporin C using such transformed host cells.

BACKGROUND OF THE INVENTION

Cephalosporin C is a natural metabolite which is obtained by fermentation of the filamentous fungus *Acremonium chrysogenum* (referred to as *A. chrysogenum* hereinbelow) on an industrial scale. This substance is an important precursor for a number of semi-synthetic cephalosporin antibiotics. The cephalosporin substance class is of great therapeutic importance. Increases in the yields of industrial cephalosporin fermentation depend essentially on continuous genetic strain improvement, in addition to improvements in process technology. More and more to the fore of modern methods of the said strain improvement is the transformation of producer strains with specific genes which have a potential for increasing production. A small group of known cephalosporin biosynthesis genes may be suspected, via the knowledge of biochemical relationships of cephalosporin biosynthesis, of having a strain improvement potential. Amplification, i.e. increasing the copy number of such known genes, indeed shows experimentally partly a significant improvement in the productivity of a producer organism. However, the group of known genes for which a strain improvement potential can be predicted from scientific plausibility assessments is very small. In addition to these known biosynthesis genes, however, an unknown number of further genes may be suspected which likewise cause a production-increasing potential by way of amplification. Frequently, the function of such genes is unknown, since there is currently still very little understanding of the entirety of cellular processes which influence cephalosporin biosynthesis. Strategies for identifying further genes with production-increasing potential are therefore of great importance.

It is thus a central object of the present invention to find such a further, hitherto unknown gene. It is thus an object of the present invention to provide a nucleic acid and vectors which code for new protein from *A. chrysogenum* and can be used for transformation of an *A. chrysogenum* host cell so that this host cell is capable of providing cephalosporin C in good yields. It is another object of the present invention to provide such a transformed host cell. Finally, it is another object of the present invention to provide a process for production of cephalosporin C using the said transformed host cell.

FIGURES

FIG. 1 shows the amino acid sequence (SEQ ID NO 1=sequence identity No. 1) of a novel *A. chrysogenum* protein, which is deduced from a nucleic acid molecule of the invention (nucleic acid sequence according to FIG. 2 or 4). The sequence is shown from the N terminus to the C terminus.

FIG. 2 (SEQ ID NO 2) shows the genomic DNA sequence, including the 3 introns of the coding region of a genomic clone of the *A. chrysogenum* gene found within the framework of the present invention from the translation start codon (ATG) to the last coding codon (TGG). The introns are underlined. The sequence is depicted in the form of a single strand in 5'-to-3' orientation.

FIG. 3 (SEQ ID NO 3) shows the cDNA sequence of the coding region of the new gene from the translation start codon (ATG) to the last coding codon (TTG); the sequence is depicted in the form of a single strand in 5'-to-3' orientation.

FIG. 4 (SEQ ID NO 4) shows the genomic DNA sequence of a BamHI/EcoR1 fragment of a genomic clone of the new gene (the sequence is depicted in the form of a single strand in 5'-to-3' orientation). The translation start codon (ATG) and the translation stop codon (TAA) of the coding region are depicted underlined and in bold type. The introns are depicted underlined.

FIG. 5 (SEQ ID NO 5) shows the *A. chrysogenum* genomic DNA sequence of an approx. 16 kb region marked by cleavage sites for SnaB1 and Bfr1, which comprises the biosynthesis genes pcbC (position 1366 to position 350, inverse arrangement) and pcbAB (position 2598 to position 13517). The sequence is depicted in the form of a single strand in 5'-to-3' orientation. The particular translation start codons and the particular translation stop codons of the corresponding coding regions are depicted underlined and in bold type. The cleavage sites mentioned are depicted underlined.

FIG. 6 (SEQ ID NO 6) shows the *A. chrysogenum* genomic DNA sequence of an approx. 5.8 kb region marked by cleavage sites for EcoRV and BamHl, which comprises the biosynthesis genes cefD1 (position 2372 to position 180, inverse arrangement) and cefD2 (position 3888 to position 5133). The sequence is depicted in the form of a single strand in 5'-to-3' orientation. The particular translation start codons and the particular translation stop codons of the corresponding coding regions are depicted underlined and in bold type. The intron in cefD2 and the cleavage sites mentioned are depicted underlined.

FIG. 7 (SEQ ID NO 7) shows the *A. chrysogenum* genomic DNA sequence of an approx. 4.6 kb region marked by cleavage sites for Xba1 and SgrAl, which comprises the biosynthesis genes cefEF (position 1118 to position 122, inverse arrangement) and cefG (position 2058 to position 3534). The sequence is depicted in the form of a single strand in 5'-to-3' orientation. The particular translation start codons and the particular translation stop codons of the corresponding coding region are depicted underlined and in bold type. The two introns in cefG and the cleavage sites mentioned are depicted underlined.

DETAILED DESCRIPTION OF THE INVENTION

A new gene in *A. chrysogenum*, which codes for a hitherto unknown protein in *A. chrysogenum*, was found within the framework of the present invention. The new gene is in its native state located approx. 5.5 kb (kilo bases) downstream (read in the direction of translation) of the known *A. chrysogenum* cefEF gene (S. E. Samson et al., Biotechnology 5 (1987), 1207-1214) on the same chromosome in the *A. chrysogenum* genome.

The new gene was found in the *A. chrysogenum* strain ATCC48272 (obtainable with this number from the ATCC, American Type Culture Collection, PO Box 1549, Manassas, Va. 20108, USA).

This strain has already been characterized in detail, for example as a producer of cephalosporins, in particular cephalosporin C (L. H. Malmberg and W. S. Hu, Appl. Microbiol. Biotechnol. 38 (1992), 122-128; Y. Q. Shen et al., Bio-Technology 4 (1986), 61-64; isopenicillin N synthetase (I. J. Hollander et al., Science 224 (1984), 610-612; J. M. Luengo et al., Bio-Technology 4 (1986), 4447); deacetoxy-cephalosporin C synthetase (Y. Q. Shen et al., Enzyme Microb. Technol. 6 (1984), 402-404); and ACV synthetase (J. Zhang et al., Curr. Microbiol. 18 (1989), 361-367; J. Zhang and A. L. Demain, Arch. Microbiol. 158 (1992), 364-369).

However, the new gene can also be found in other *A. chrysogenum* strains and be isolated therefrom. Alternatively, the nucleic acid and amino acid sequences or molecules presented herein may be synthesized, in particular chemically synthesized.

The gene codes for a protein of 526 amino acids in length (see FIG. 1, SEQ ID NO 1). The amino acid sequence is depicted in FIG. 1. The coding region in the gene is interrupted by 3 introns, as FIGS. 2 and 4 show.

The present invention thus relates to an isolated nucleic acid molecule which codes for a protein comprising the amino acid sequence according to SEQ ID NO 1 (see FIG. 1).

A nucleic acid molecule of this type may thus code, for example, for a protein which comprises, in addition to the amino acid sequence listed (SEQ ID NO 1), still further amino acids, for example for a fusion protein. Such fusion proteins may play a part, for example, if preparation of the new protein in isolated form is desired. The fusion parts can increase stability or facilitate purification, for example.

Within the framework of the present invention, preference is given to a nucleic acid molecule of the invention, which codes only or exclusively for an amino acid sequence according to SEQ ID NO 1. A nucleic acid molecule of this type may advantageously be employed for the purpose of producing cephalosporin C, described hereinbelow. The present invention thus further relates to a nucleic acid molecule of the invention, which codes for a protein consisting of the amino acid sequence according to SEQ ID NO 1.

A nucleic acid molecule of the invention is preferably a DNA molecule, in particular an isolated genomic DNA molecule or a corresponding cDNA molecule. A cDNA molecule may be prepared, for example, by reverse transcription of a corresponding mRNA molecule or synthetically. Alternatively, the nucleic acid molecule may be an RNA molecule, in particular an mRNA molecule.

The DNA molecule of the invention may be prepared, for example, by generating a genomic DNA library of the genome of the said *A. chrysogenum* strain ATCC48272. A genomic clone is identified which contains the known *A. chrysogenum* cefEF gene and additionally at least about 10 kb of sequence downstream of the cefEF gene. This may be carried out by screening with homologous probes whose structures can be deduced from the known nucleic acid sequence of the cefEF gene (S. E. Samson et al., see above). Appropriate techniques are known from the literature (e.g. in T. Maniatis et al., Molecular Cloning—A Laboratory Manual, 1982, Cold Spring Harbor Laboratory, Cold Spring Harbor, N.Y., USA). The desired DNA molecule is located on an approx. 2.5 kb EcoRl/BamHl fragment of such a clone, which fragment can be isolated or prepared using classical techniques. FIG. 4 depicts such a fragment. A preferred embodiment of the present invention thus relates to a nucleic acid molecule of the invention, comprising a base sequence according to SEQ ID NO 4 or a base sequence which differs from the sequence according to SEQ ID NO 4 only due to the degeneracy of the genetic code. That is to say, according to the invention the present invention also relates to those nucleic acid molecules which differ from the specifically listed sequences by one or more of the codons listed being replaced by one or more other codons in such a way that the amino acid sequence of the encoded protein (SEQ ID NO 1) is not altered.

This also applies to the further nucleic acid molecules described below. The nucleic acid molecule according to SEQ ID NO 4 contains regulatory sequences (such as a promoter and a stop codon) and may be used advantageously, in particular in a vector, for transformation of *A. chrysogenum* and thus for production of cephalosporin C.

The mentioned EcoRl/BamHl fragment of 2.5 kb comprises in particular the coding part of the new gene. This part is depicted in FIG. 2 and comprises 3 introns. The present invention thus further relates to a nucleic acid molecule of the invention, comprising a base sequence according to SEQ ID NO 2 or a base sequence which differs from the sequence according to SEQ ID NO 2 only due to the degeneracy of the genetic code, as discussed above. A nucleic acid molecule of this type thus corresponds to the genomic DNA sequence of the coding part of the new gene. Further preferred embodiments of the present invention are those nucleic acid molecules which differ from that of SEQ ID NO 2 by the absence of one, two or all three introns.

Therefore, preference is furthermore given to a nucleic acid molecule of the invention, comprising a base sequence according to SEQ ID NO 3 or a base sequence which differs from the sequence according to SEQ ID NO 3 due to the degeneracy of the genetic code, as discussed above. A nucleic acid molecule of this type no longer comprises any of the introns mentioned and as such can be equated with a corresponding cDNA sequence.

A nucleic acid molecule of the invention (including a cDNA molecule mentioned) may furthermore, for example, be fully or partly synthesized. RNA or mRNA molecules of the invention can be isolated from the microorganism *A. chrysogenum* by means of standard techniques or can be produced synthetically. It is possible to prepare from an appropriate mRNA a corresponding cDNA molecule, using standard techniques.

While it is perfectly possible for the said nucleic acid molecules to contain further base sequences (in order to code for a fusion protein, for example), preferred embodiments relate to a nucleic acid molecule of the invention which exclusively or solely consists of a base sequence selected from the group of the base sequences SEQ ID NO 2, SEQ ID NO 3, SEQ ID NO 4 and a base sequence which differs from any of the said sequences only due to the degeneracy of the genetic code, as discussed above.

In another embodiment nucleic acid molecules of the invention additionally comprise, immediately after the end of the coding region (corresponding to the C terminus of the encoded protein), one or more stop codon(s). Preference is given to the naturally occurring stop codon which has been identified as TAA. The other stop codons may also be used, however.

Owing to similarities with other, known protein sequences, the protein (SEQ ID NO 1) encoded by the nucleic acid molecules of the invention may be characterized as a hydrolase, in particular as a acetyl-CoA hydrolase, although this should not be construed as being limiting. The principal concern of the present invention, however, is not the description of the function of the new protein but, in particular, the use of the new gene or the use of the nucleic acid molecules of the invention which code for the new protein in order to transform, preferably, *A. chrysogenum* host strains, in particular for the purpose of producing cephalosporin C, this being illustrated in more detail below.

The present invention furthermore relates to a vector comprising any of the mentioned nucleic acid molecules of the invention. Preferably, such a vector is suitable for transformation of a host cell. Such a host cell is in particular a microorganism, in particular *A. chrysogenum*. Such a vector may be in the form of a plasmid, for example, and contains, where necessary, in addition to a nucleic acid molecule of the invention further sequences, for example an origin of replication and further regulatory elements (promoter, transcription termination signal, translation start signal, translation termination signal, etc.) so that, after transformation has been carried out, expression of the nucleic acid molecule of the invention can take place. After transformation has been carried out, a nucleic acid molecule of the invention and also other vector elements may integrate into the genome of the host cell, amounting to an amplification of the coding part of the new gene. A vector of the invention advantageously comprises a nucleic acid molecule comprising a base sequence according to SEQ ID NO 4. Such a base sequence corresponds to the EcoRl/BamHl fragment mentioned and already comprises regulatory sequences such as, for example, a corresponding promoter.

Vectors of this type may be generated according to standard techniques by cloning a nucleic acid molecule of the invention into suitable standard vectors.

In addition to the nucleic acid molecules described which derive from the newly found gene, a vector of the invention may, in particular, contain one or more further nucleic acid molecule(s) derived from genes which are already known and which are involved in cephalosporin biosynthesis in *A. chrysogenum*, with particular mention being made of pcbAB (S. Gutierrez, J. Bacteriol. 173 (1991), pp. 2354-2365), pcbC (S. Gutierrez, J. Bacteriol. 173 (1991), pp. 2354-2365), cef D1 (R. V. Ullan et al., J. Biol. Chem. 277 (2002) pp. 46216-46225), cefD2 (R. V. Ullan et al., J. Biol. Chem. 277 (2002) pp. 46216-46225), cefEF (S. Gutierrez, J. Bacteriol. 174 (1992), pp. 3056-3064) and cefG (S. Gutierrez, J. Bacteriol. 174 (1992), pp. 3056-3064).

Thus, in another preferred embodiment, a vector of the invention, as described above, additionally comprises at least one further nucleic acid molecule coding for a protein selected from the group of proteins encoded by the following *Acremonium chrysogenum* genes: pcbAB, pcbC, cefD1, cefD2, cefEF and cefG.

Preferably, a vector of the invention additionally comprises two further nucleic acid molecules coding for the proteins correspondingly encoded by the *Acremonium chrysogenum* genes pcbAB and pcbC, respectively.

Furthermore, a vector of the invention preferably additionally comprises two further nucleic acid molecules coding for the proteins correspondingly encoded by the *Acremonium chrysogenum* genes cefD1 and cefD2, respectively.

Furthermore, a vector of the invention preferably additionally comprises two further nucleic acid molecules coding for the proteins correspondingly encoded by the *Acremonium chrysogenum* genes cefEF and cefG, respectively.

The pcbAB sequence to be used preferably corresponds to the nucleotide sequence to be found in FIG. 5. The pcbC sequence to be used preferably corresponds to the nucleotide sequence which is likewise to be found in FIG. 5. The cefD1 sequence to be used preferably corresponds to the nucleotide sequence to be found in FIG. 6. The cefD2 sequence to be used preferably corresponds to the nucleotide sequence which is likewise to be found in FIG. 6. The cefEF sequence to be used preferably corresponds to the nucleotide sequence to be found in FIG. 7. The cefG sequence to be used preferably corresponds to the nucleotide sequence which is likewise to be found in FIG. 7.

The present invention further relates to a host cell which has been transformed with a vector of the invention, which vector comprises the new nucleic acid molecule of the invention and additionally, where appropriate, further nucleic acid molecules, as described above. The host cell is preferably a microorganism, in particular *A. chrysogenum*.

A host cell of this type, in particular one of *A. chrysogenum*, is transformed with a vector of the invention according to standard methods. Such a method is described, for example, in C. Nowak and U. Kück, Curr. Genet. 25 (1994), pp. 34-40.

Advantageously, a transformed *A. chrysogenum* host cell of the invention may be used for production of cephalosporin C. The present invention thus also relates to a process for production of cephalosporin C, comprising culturing of an *A. chrysogenum* host cell of the invention under conditions suitable for effecting production of cephalosporin C by the host cell.

Suitable culturing/fermentation techniques, for example in particular for *A. chrysogenum*, are known to the skilled worker in the field of antibiotics and have been employed in production of cephalosporin C for a long time.

In a preferred embodiment the process of the invention furthermore comprises isolation of the cephalosporin C produced. Cephalosporin C produced by a transformed *A. chrysogenum* host cell of the invention is usually secreted by the microorganism and can be purified or isolated from the culture supernatant by known techniques, for example chromatographic techniques.

Cephalosporin C generated according to the invention may preferably be reacted to give further derivatives with antibiotic properties.

An alternative application of the present invention relates to an isolated protein comprising an amino acid sequence according to SEQ ID NO 1. Such a protein also comprises, as mentioned, corresponding fusion proteins from which, where desired, a mature protein with an amino acid sequence according to SEQ ID NO 1 can be generated by cleaving. Preference is given to a protein of the invention, which exclusively or solely consists of the amino acid sequence according to SEQ ID NO 1.

A protein of the invention may be produced by culturing a suitable prokaryotic or eukaryotic host cell containing a suitable expression vector of the invention, which vector comprises a nucleic acid molecule coding for the said protein, under conditions leading to expression of the said protein. The protein may be purified and isolated using common techniques. Examples of suitable prokaryotic host cells in which, in particular, a cDNA of the invention is used are bacterial cells, e.g. *E. coli*; examples of suitable eukaryotic host cells are mammalian cells such as, for example, CHO or BHK cells.

Such proteins of the invention may be used in isolated form, for example in the synthetic or semi-synthetic production of cephalosporin C or derivatives thereof. An example of common practice would be the immobilization on a synthesis column on which a reaction takes place.

The references mentioned herein are herewith in their entirety incorporated by reference.

The present invention is illustrated in more detail by the examples below but is not limited thereto. The examples relate in particular to preferred embodiments of the present invention.

EXAMPLES

The materials and reagents mentioned herein are familiar to the skilled worker, commercially available or readily accessible and can be used according to the manufacturer's instructions.

Example 1

Identification of a New Gene and a New Protein from *A. chrysogenum*

DNA sequences for the cephalosporin biosynthesis genes and flanking sequences may be constructed with the aid of lambda clones. Such lambda clones can be isolated from a lambda gene bank containing DNA inserts of *A. chrysogenum* ATCC48272. The construction of lambda gene banks is mentioned, for example, in T. Maniatis et al. (see above), as is the screening of lambda gene banks by means of lambda-plaque hybridization. The DNA sequence information on cephalosporin biosynthesis genes from *A. chrysogenum*, required for this screening, can be made available by means of database searches (e.g. GENBANK). Examples of search terms suitable for this database request are the names for an appropriate biosynthesis gene (cefEF) which is to be present on the clone searched for. Cloning of the gene found within the framework of the present invention may start out from a lambda clone which is identified by means of plaque hybridization using sequence information of the cefEF gene, provided that this clone contains a DNA insert of at least about 10 kb of DNA sequence downstream of the stop codon of the cefEF gene. A BamHl/EcoRl restriction fragment of about 2.5 kb which fully includes the gene of the invention and thus, in particular, the nucleic acid molecules of the invention according to SEQ ID NO 2 and SEQ ID NO 4 is essential for subsequent cloning. This fragment can be identified, for example, by PCR using the primers PCR1f and PCR1r which are defined by the following sequences:

```
                                           (SEQ ID NO 8)
    Primer PCR1f 5'- TTT GGG CGA GTG GGC TAA TA (SEQ ID NO 9)
    Primer PCR1r 5'- CAA CAA CGC CTC TCC CGT CT
```

In order to clone the newly found gene or the nucleic acid molecules of the invention, the BamHl/EcoRl restriction fragment of about 2.5 kb is cloned into the vector pCN3 (described in Nowak and Kück, see above). This vector is distinguished by a modified tubulin resistance gene (Nowak and Kück, see above) which allows selection of *Acremonium* transformants. The unique EcoRl cleavage site on pCN3 is utilized for cloning. A ligation is carried out in three steps:
1) ligating the two DNA molecules in each case via a compatible EcoRl cleavage site
2) adapting the protruding ends with Klenow enzyme
3) linking the modified ends by further ligation The ligation product is transformed into *E. coli* (e.g. DH5alpha strain) and produced there in an amount sufficient for the further transformation steps and purified. Due to the way of construction, it is also possible to obtain plasmids which contain the nucleic acid molecule in inverse orientation; in principle, however, these structures have the same functionality. *E. coli* clones containing the desired plasmid can be identified by PCR using the PCR primers mentioned, PCR1f and PCR1r; the resulting PCR product is 2.5 kb in length. These PCR analyses may be carried out using the Expand High Fidelity PCR system from Roche Applied Science, according to the specifications for the PCR reaction which are also supplied. Subsequent sequencing and evaluation results in the nucleic acid sequences depicted in FIGS. 2 (SEQ ID NO 2) and 4 (SEQ ID NO 4). A cDNA sequence according to FIG. 3 (SEQ ID NO 3) and also the amino acid sequence of the encoded protein according to FIG. 1 (SEQ ID NO 1) can then be deduced therefrom. In principle, it is possible to finally verify the cloning product by sequencing and sequence comparison with the DNA sequences depicted in FIGS. 2 and 4. A plasmid carrying the EcoRl/BamH fragment is referred to as plasmid 1 and used below.

Example 2

Transformation of *A. chrysogenum*

Plasmid 1 is transformed into *A. chrysogenum* ATCC48272 (see above) by means of a standard procedure for protoplast transformation. These methods are described, for example, in Nowak and Kück (see above) and involve selection of transformants on benomyl-containing nutrient agar. The properties of the modified tubulin gene CA_Tubulin (Tyr) on plasmid 1 and, respectively, pCN3, used for this selection, is described in Nowak and Kück (see above), as is the benomyl-containing nutrient agar required for selection. Transformants from this type of experiments can be assayed, for example by means of PCR, for the presence of the essential parts of plasmid 1. The PCR primers below allow such assaying:

```
                                          (SEQ ID NO 10)
    Primer PCR2f 5'- GCA GAG CGC AGA TAC CAA (SEQ ID NO 11)
    Primer PCR2r 5'- CGT GGA CTC CAA CGT CAA
```

The resulting PCR product is 8 279 bp in length. The PCR analyses may be carried out, for example, by means of the Expand Long Template PCR system from Roche Applied Science, according to the specifications for the PCR reaction which are also supplied.

Sensibly, a population of transformants with pCN3 is provided for control purposes in addition to a population of transformants with plasmid 1. These transformants can be analysed in PCR reaction mixtures using the following PCR primers:

```
                                          (SEQ ID NO 12)
    Primer PCR3f 5'- TTC CAT CCA GCA CCT CAC (SEQ ID NO 13)
    Primer PCR3r 5'- CTT AAT GCG CCG CTA CAG
```

The resulting PCR product is 2 290 bp in length.

Example 3

Production and Isolation of Cephalosporin C

The transformants generated in Example 2 are tested for cephalosporin production in flask fermentation experiments. Sensibly, in each case a population of about the same size of approx. 500 transformants with plasmid 1 and of control transformants with pCN3 is compared in parallel. To this end, supernatants of these flask fermentations are evaluated by means of HPLC analysis. A corresponding method, including the accompanying analysis, is described, for example, in L. Karaffa et al., Appl. Microbiol. Biotechnol. 51 (1999), 633-638. In order to obtain statistically relevant amounts of data, these analyses are repeated several times (e.g. 6 times), with each repeat comprising in each case several (e.g. 4) parallel flask fermentations of each strain which are individually tested. It turns out that it is possible to identify in this way strains which originate from the transformation with plasmid 1 and which have reproducibly a distinctly higher cephalosporin productivity than the population of pCN3 control transformants in comparison therewith.

The HPLC columns used in the said analysis may also be used in the purification and isolation of cephalosporin C produced.

Example 4

Construction of Plasmid 2 Comprising the *A. chrysogenum* Genes cefD1 and cefD2

Plasmid 1 of Example 1 is subsequently extended by the two cephalosporin biosynthesis genes cefD1 and cefD2. These genes are described in R. V. Ullan, J. Biol. Chem. 277 (2002), pp. 46216-46225. Both genes are located in close proximity on a 5.8 kb EcoRV/BamHl fragment and are provided with the aid of suitable lambda clones. Such lambda clones are isolated from a lambda gene bank containing DNA inserts of *Acremonium chrysogenum* ATCC48272. The construction of lambda gene banks is mentioned, for example, in T. Maniatis et al. (see above), as is the screening of lambda gene banks by means of lambda-plaque hybridization. The DNA sequence information of the biosynthesis genes cefD1 and cefD2, required for this screening, can be made available, for example, by means of database requests (e.g. GEN-BANK). Examples of search terms suitable for this database request are the names of the two biosynthesis genes (cefD1, cefD2). Cloning of the two biosynthesis genes starts out from a lambda clone which is identified by means of plaque hybridization using sequence information of the cefD1 and cefD2 genes, the said clone containing a DNA insert of at least 6 kb of DNA sequence. A BamHl/EcoRV restriction fragment of about 5.8 kb which comprises the two complete biosynthesis genes cefD1 and cefD2 is essential for subsequent cloning. This fragment can be identified by PCR using the primers PCR4f and PCR4r which are defined by the following sequences:

```
                                         (SEQ ID NO 14)
Primer PCR4f 5'- ATC TGA GTG GTT GTT CCG CG (SEQ ID NO 15)
Primer PCR4r 5'- CGA GGA TGA AGA CGG TGA AA
```

Plasmid 1 of Example 1 is extended by cloning the BamHl/EcoRV restriction fragment of about 5.8 kb according to SEQ ID NO 6, containing the two biosynthesis genes cefD1 and cefD2, into plasmid 1. The unique SmaI cleavage site on plasmid 1 is utilized for cloning. The two protruding ends of the 5.8 kb BamHl/EcoRV restriction fragment are adapted with Klenow enzyme and ligated with the SmaI-cleaved plasmid 1.

The ligation product is transformed into *E. coli* (e.g. DH5alpha strain) and produced there in an amount sufficient for the further transformation steps and purified. Due to the way of construction, it is also possible to obtain plasmids which contain the nucleic acid molecule in inverse orientation; in principle, however, these structures have the same functionality. *E. coli* clones containing the desired plasmid can be identified by PCR using the PCR primers mentioned, PCR4f and PCR4r; the resulting PCR product is 5.5 kb in length. These PCR analyses may be carried out using the Expand High Fidelity PCR system from Roche Applied Science, according to the specifications for the PCR reaction which are also supplied. In principle, it is possible to finally verify the cloning product by sequencing and sequence comparison with the DNA sequence depicted in FIG. 6. A plasmid carrying the BamHl/EcoRV fragment is referred to as plasmid 2 and used below.

Example 5

Construction of Plasmid 3 Comprising the *A. chrysogenum* Genes pcbAB and pcbC Plasmid 1 of Example 1 is subsequently extended by the two cephalosporin biosynthesis genes pcbAB and pcbC to give plasmid 3. In nature, the genes pcbAB and pcbC are present in a genetically closely coupled form as biosynthesis gene cluster I and are described in S. Gutierrez, J Bacteriol. 173 (1991), pp. 2354-2365. Both genes are located in close proximity on an approx. 16 kb SnaBl/Bfrl fragment and are provided with the aid of suitable lambda clones. Such lambda clones are isolated from a lambda gene bank containing DNA inserts of *Acremonium chrysogenum* ATCC48272. The construction of lambda gene banks is mentioned, for example, in T. Maniatis et al. (see above), as is the screening of lambda gene banks by means of lambda-plaque hybridization. The DNA sequence information of the biosynthesis genes pcbAB and pcbC, required for this screening, can be made available, for example, by means of database requests (e.g. GEN-BANK). Examples of search terms suitable for this database request are the names of the two biosynthesis genes (pcbAB, pcbC). Cloning of the two biosynthesis genes starts out from a lambda clone which is identified by means of plaque hybridization using sequence information of the pcbAB and pcbC genes, the said clone containing a DNA insert of at least 16 kb of DNA sequence. A SnaBl/Bfrl restriction fragment of about 16 kb which comprises the two complete biosynthesis genes pcbAB and pcbC is essential for subsequent cloning. This fragment can be identified by PCR using the primers PCR5f and PCR5r which are defined by the following sequences:

```
                                         (SEQ ID NO 16)
Primer PCR5f 5'- AGG AGA GGC CGA AGA CGT CCC AGT A (SEQ ID NO 17)
Primer PCR5r 5'- TTT CGC TTA GGG CTC GGA CGC T
```

Plasmid 1 of Example 1 is extended by cloning the SnaBl/Bfrl restriction fragment of approx. 16 kb according to SEQ ID NO 5, containing the two biosynthesis genes pcbAB and pcbC, into plasmid 1. The unique SmaI cleavage site on plasmid 1 is utilized for cloning. The two protruding ends of the approx. 16 kb SnaBl/Bfrl restriction fragment are adapted with Klenow enzyme and ligated with the SmaI-cleaved plasmid 1.

The ligation product is transformed into *E. coli* (e.g. DH5alpha strain) and produced there in an amount sufficient for the further transformation steps and purified. Due to the way of construction, it is also possible to obtain plasmids which contain the nucleic acid molecule in inverse orientation; in principle, however, these structures have the same functionality. *E. coli* clones containing the desired plasmid can be identified by PCR using the PCR primers mentioned, PCR5f and PCR5r; the resulting PCR product is 10.5 kb in length. These PCR analyses may be carried out using the Expand High Fidelity PCR system from Roche Applied Science, according to the specifications for the PCR reaction which are also supplied. In principle, it is possible to finally verify the cloning product by sequencing and sequence comparison with the DNA sequence depicted in FIG. 5. A plasmid carrying the SnaBl/Bfrl fragment is referred to as plasmid 3 and used below.

Example 6

Construction of Plasmid 4 Comprising the *A. chrysogenum* Genes cefEF and cefG Plasmid 1 of Example 1 is subsequently extended by the two cephalosporin biosynthesis genes cefEF and cefG to give plasmid 4. In nature, the genes cefEF and cefG are present in a genetically closely coupled form as biosynthesis gene cluster II and are described in S. Gutierrez, J. Bacteriol. 174 (1992), pp. 3056-3064. Both genes are located in close proximity on an approx. 4.6 kb Xbal/SgrAl fragment and are provided with the aid of suitable lambda clones. Such lambda clones are isolated from a lambda gene bank containing DNA inserts of *Acremonium chrysogenum* ATCC48272. The construction of lambda gene banks is mentioned, for example, in T. Maniatis et al. (see above), as is the screening of lambda gene banks by means of lambda-plaque hybridization. The DNA sequence information of the biosynthesis genes cefEF and cefG, required for this screening, can be made available, for example, by means of database requests (e.g. GEN-BANK). Examples of search terms suitable for this database request are the names of the two biosynthesis genes (cefEF, cefG). Cloning of the two biosynthesis genes starts out from a lambda clone which is identified by means of plaque hybridization using sequence information of the cefEF and cefG genes, the said clone containing a DNA insert of at least 4.6 kb of DNA sequence. A Xbal/SgrAl restriction fragment of about 4.6 kb which comprises the two complete biosynthesis genes cefEF and cefG is essential for subsequent cloning. This fragment can be identified by PCR using the primers PCR6f and PCR6r which are defined by the following sequences:

```
                                      (SEQ ID NO 18)
Primer PCR6f 5'- TCG GGA GGT GGA GGA ATT CT (SEQ ID NO 19)
Primer PCR6r 5'- ATC TTG CGC GCT GTT TCG AG
```

Plasmid 1 of Example 1 is extended by cloning the Xbal/SgrAl restriction fragment of approx. 4.6 kb containing the two biosynthesis genes cefEF and cefG, into plasmid 1. The unique Smal cleavage site on plasmid 1 is utilized for cloning. The two protruding ends of the 4.6 kb Xbal/SnaBl restriction fragment are adapted with Klenow enzyme and ligated with the Sma1-cleaved plasmid 1.

The ligation product is transformed into *E. coli* (e.g. DH5alpha strain) and produced there in an amount sufficient for the further transformation steps and purified. Due to the way of construction, it is also possible to obtain plasmids which contain the nucleic acid molecule in inverse orientation; in principle, however, these structures have the same functionality. *E. coli* clones containing the desired plasmid can be identified by PCR using the PCR primers mentioned, PCR6f and PCR6r; the resulting PCR product is 2.5 kb in length. These PCR analyses may be carried out using the Expand High Fidelity PCR system from Roche Applied Science, according to the specifications for the PCR reaction which are also supplied. In principle, it is possible to finally verify the cloning product by sequencing and sequence comparison with the DNA sequence depicted in FIG. 7. A plasmid carrying the Xbal/SgrAl fragment is referred to as plasmid 4 and used below.

Example 7

Transformation of *A. chrysogenum* with Plasmid 2

Transformation with plasmid 2 is illustrated below; however, it is also possible to use plasmid 3 and plasmid 4 accordingly and with comparable results (Examples 9 and 10).

Plasmid 2 is transformed into an *A. chrysogenum* strain (CEF-67605) by means of a standard procedure for protoplast transformation, it also being possible to use available *A. chrysogenum* strains such as ATCC48272 (see above) as alternatives. These methods are described, for example, in Nowak and Kück (see above) and involve selection of transformants on benomyl-containing nutrient agar. Nowak and Kück (see above) describe the properties of the modified tubulin gene CA_Tubulin(Tyr) used for this selection on plasmid 1 and, respectively, pCN3 and also the benomyl-containing nutrient agar required for selection. Transformants from such experiments are assayed for the presence of the essential parts of plasmid 2 by means of PCR. The PCR primers below allow such assaying:

```
                                      (SEQ ID NO 20)
Primer PCR7f 5'- GGG GCG GAG CCT ATG GAA AA (SEQ ID NO 21)
Primer PCR7r 5'- TCC AGC TCA CCT TGC TCC AG
```

The resulting PCR product is 9 001 bp in length. The PCR analyses may be carried out, for example, by means of the Expand Long Template PCR system from Roche Applied Science, according to the specifications for the PCR reaction which are also supplied.

Sensibly, a population of transformants with pCN3 is provided for control purposes in addition to a population of transformants with plasmid 2. These transformants can be analysed in PCR mixtures using the following PCR primers:

```
                                      (SEQ ID NO 12)
Primer PCR3f 5'- TTC CAT CCA GCA CCT CAC (SEQ ID NO 13)
Primer PCR3r 5'- CTT AAT GCG CCG CTA CAG
```

The resulting PCR product is 2 290 bp in length.

Example 8

Production and Isolation of Cephalosporin C from a Transformed Strain According to Example 7

The transformants generated in Example 7 are assayed as described in Example 3 and cephalosporin C is purified accordingly.

Among 550 transformants analysed, 7 strains (e.g. strain CET-98118) are found, whose cephalosporin C titre has increased by up to 10% in comparison with the non-trans-

Example 9

Transformation of *A. chrysogenum* with Plasmid 3 and Subsequent Production and Isolation of Cephalosporin C Similarly to Example 7, an *A. chrysogenum* strain (CEF-67605) is transformed with plasmid 3, it also being possible to use available *A. chrysogenum* strains such as ATCC48272 as alternatives.

The transformants generated in this way are assayed as described in Example 3 and cephalosporin C is purified accordingly. Strains which have increased cephalosporin C titres in comparison with the non-transformed starting strain may be used for production purposes on an industrial scale.

Example 10

Transformation of *A. chrysogenum* with Plasmid 4 and Subsequent Production and Isolation of Cephalosporin C Similarly to Example 7, an *A. chrysogenum* strain (CEF-67605) is transformed with plasmid 4, it also being possible to use available *A. chrysogenum* strains such as ATCC48272 (see above) as alternatives.

The transformants generated in this way are assayed as described in Example 3 and cephalosporin C is purified accordingly. Strains which have increased cephalosporin C titres in comparison with the non-transformed starting strain may be used for production purposes on an industrial scale.

---

What is claimed is:

1. An isolated nucleic acid molecule which encodes a protein comprising the amino acid sequence according to SEQ ID NO 1.

2. The nucleic acid molecule according to claim 1, which encodes a protein consisting of the amino acid sequence according to SEQ ID NO 1.

3. The nucleic acid molecule according to claim 1, which is a DNA molecule.

4. The nucleic acid molecule according to claim 3, comprising the nucleotide sequence according to SEQ ID NO 2 or a nucleotide sequence which differs from the sequence according to SEQ ID NO 2 only due to the degeneracy of the genetic code.

5. The nucleic acid molecule according to claim 3, consisting of the nucleotide sequence according to SEQ ID NO 3.

6. The nucleic acid molecule according to claim 3, comprising the nucleotide sequence according to SEQ ID NO 4 or a nucleotide sequence which differs from the sequence according to SEQ ID NO 4 only due to the degeneracy of the genetic code.

7. The nucleic acid molecule according to claim 3, consisting of a nucleotide sequence selected from the group consisting of SEQ ID NO 2, SEQ ID NO 3, SEQ ID NO 4 and a nucleotide sequence which differs from any of the said nucleotide sequences only due to the degeneracy of the genetic code.

8. A vector comprising a nucleic acid molecule according to claim 1.

9. The vector according to claim 8, additionally comprising at least one further nucleic acid molecule encoding a protein selected from the group of proteins encoded by the following *Acremonium chrysogenum* genes: pcbAB, pcbC, cefD1, cefD2, cefEF and cefG.

10. The vector according to claim 8, additionally comprising two further nucleic acid molecules encoding the proteins encoded by the *Acremonium chrysogenum* genes: pcbAB and pcbC, respectively.

11. The vector according to claim 8, additionally comprising two further nucleic acid molecules encoding the proteins encoded by the *Acremonium chrysogenum* genes: cefD1 and cefD2, respectively.

12. The vector according to claim 8, additionally comprising two further nucleic acid molecules encoding the proteins encoded by the *Acremonium chrysogenum* genes: cefEF and cefG, respectively.

13. The vector according to claim 8, which is suitable for transformation of a host cell.

14. The vector according to claim 13, wherein the host cell is a microorganism.

15. The vector according to claim 14, wherein the microorganism is *Acremonium chrysogenum*.

16. An isolated host cell which has been transformed with a vector according to claim 8.

17. The host cell according to claim 16, which is a microorganism.

18. The host cell according to claim 17, wherein the microorganism is *Acremonium chrysogenum*.

19. A process for production of cephalosporin C, comprising culturing of a host cell according to claim 18 under conditions suitable for effecting production of cephalosporin C by the host cell.

20. The process according to claim 19, further comprising isolation of the cephalosporin C produced.

21. An isolated protein comprising the amino acid sequence according to SEQ ID NO 1.

22. The protein according to claim 21, consisting of the amino acid sequence according to SEQ ID NO 1.

* * * * *

SEQUENCE LISTING

```
<160> NUMBER OF SEQ ID NOS: 21

<210> SEQ ID NO 1
<211> LENGTH: 526
<212> TYPE: PRT
<213> ORGANISM: Acremonium chrysogenum

<400> SEQUENCE: 1

Met Ala Ser Pro Ile Ala Ser Ala Ala Leu Lys Ala Arg Ile Arg Arg
1               5                   10                  15

Pro Ser Met Leu Lys Lys Leu Cys Lys Pro Gln Asp Leu Met His His
            20                  25                  30

Phe Pro Asn Gly Ser Tyr Ile Gly Trp Ser Gly Phe Thr Gly Val Gly
        35                  40                  45

Tyr Pro Lys Lys Met Pro Thr Tyr Met Ala Asp His Val Glu Gln Asn
    50                  55                  60

Gly Leu Gln Gly Lys Leu Lys Tyr Ser Leu Phe Val Gly Ala Ser Ser
65                  70                  75                  80

Gly Ala Glu Thr Glu Asn Arg Trp Ala Ser Leu Asp Met Ile Asp Arg
                85                  90                  95

Arg Thr Pro His Gln Val Gly Lys Ala Ile Ser Lys Gly Ile Asn Glu
            100                 105                 110

Gly Lys Ile His Phe Phe Asp Lys His Leu Ser Met Phe Pro Val Asp
        115                 120                 125

Leu Val Tyr Gly Tyr Tyr Thr Lys Asp Arg Pro His Asn Lys Leu Asp
    130                 135                 140

Val Val Val Val Glu Ala Thr Asp Ile Lys Glu Asp Gly Ser Ile Val
145                 150                 155                 160

Pro Gly Ala Ser Val Gly Ala Thr Pro Glu Leu Ile Gln Met Ala Asp
                165                 170                 175

Lys Ile Ile Ile Glu Val Asn Thr Ser Leu Pro Ser Phe Glu Gly Leu
            180                 185                 190

His Asp Ile Thr Met Thr Asp Leu Pro Pro Leu Arg Lys Pro Tyr Leu
        195                 200                 205

Val Met Gly Val Glu Asp Arg Ile Gly Arg Thr Ser Ile Pro Ile Asp
    210                 215                 220

Pro Glu Lys Val Val Gly Ile Leu Glu Ser Asp Tyr Gln Asp Ala Thr
225                 230                 235                 240
```

```
Ala Pro Asn Ala Glu Ala Asp Glu Ser Ala Asn Lys Ile Ala Gly His
                245                 250                 255

Leu Ile Glu Phe Phe Glu His Glu Val Ala His Gly Arg Leu Pro Asn
            260                 265                 270

Ser Leu Leu Pro Leu Gln Ser Gly Ile Gly Asn Val Ala Asn Ala Ile
        275                 280                 285

Ile Gly Gly Leu Asp Asn Ser Asn Phe Arg Asn Leu Lys Val Trp Thr
    290                 295                 300

Glu Val Ile Gln Asp Thr Phe Leu Asp Leu Phe Asp Ser Gly Arg Leu
305                 310                 315                 320

Asp Phe Ala Thr Ala Thr Ser Ile Arg Phe Ser Pro Asp Gly Phe Arg
                325                 330                 335

Arg Phe Tyr Asp Asn Trp Glu Ala Tyr Tyr Gly Lys Leu Leu Leu Arg
            340                 345                 350

Ser Gln Gln Val Ser Asn Ser Pro Glu Ile Ile Arg Arg Leu Gly Val
        355                 360                 365

Ile Ala Met Asn Thr Pro Val Glu Val Asp Ile Tyr Ala His Ala Asn
    370                 375                 380

Ser Thr Cys Val Met Gly Ser Arg Met Leu Asn Gly Leu Gly Gly Ser
385                 390                 395                 400

Ala Asp Phe Leu Arg Ser Ser Lys Tyr Ser Ile Met His Thr Pro Ser
                405                 410                 415

Thr Arg Pro Ser Lys Thr Asp Pro His Gly Val Ser Cys Ile Val Pro
            420                 425                 430

Met Cys Thr His Ile Asp Gln Thr Glu His Asp Leu Asp Val Ile Val
        435                 440                 445

Thr Glu Gln Gly Leu Ala Asp Val Arg Gly Leu Ser Pro Arg Glu Arg
    450                 455                 460

Ala Arg Val Ile Ile Lys Lys Cys Ala His Pro Val Tyr Gln Pro Ile
465                 470                 475                 480

Leu Thr His Tyr Phe Glu Lys Ala Glu Ser Asp Cys Leu Arg Lys Gly
                485                 490                 495

Trp Gly His Glu Pro His Leu Leu Phe Asn Ser Phe Asp Leu His Lys
            500                 505                 510

Ala Leu Val Glu His Gly Ser Met Gln Lys Val Gly Gln Trp
        515                 520                 525

<210> SEQ ID NO 2
<211> LENGTH: 1765
<212> TYPE: DNA
<213> ORGANISM: Acremonium chrysogenum

<400> SEQUENCE: 2
atggcatcac caatagcctc tgccgccctc aaggcgcgca ttcgccgccc ctcgatgctc      60
aagaagctgt gcaagcccca ggatttgatg catcacttcc ccaatggctc gtacattggc     120
tggtccggct tcaccggcgt cggctacccg aagtgagttc caccgtcatc ccgctccaca     180
gtaggcgcag ccggcccgct gacagtcccc gacaggaaaa tgccgaccta catggccgat     240
cacgtcgagc agaacggcct tcagggcaag ctgaagtact cgctattcgt gggcgcatcg     300
tcgggtgctg agacagagaa tcgctgggcg tcgctcgaca tgattgatag gaggaccccg     360
catcaggtcg gcaaggccat ctccaagggc atcaatgagg caagatcca  cttcttcgac     420 aagcatctct ccatgttccc cgtggacctt gtatacgtac gtcaacgatg atcccttgga     480
```

```
atgtgcatgt actacgagta cctggcgcta acatccggtc agggctacta cacaaaggat      540
agaccccaca acaagctgga cgtggtggtg gtggaggcca ccgacatcaa agaggacgga      600
agcattgtac ccggagcttc agtcggcgcg acccccgagc tcatccagat ggccgataag      660
gtgagcaatt tcgatttcta gcggagggcg cagcaggacc tgacatctcc ctgtgcagat      720
cattatcgag gtcaacacct cactgccttc attcgagggt ctccacgaca tcaccatgac      780
cgacctgccc ccgctacgga agccctatct cgtcatgggt gtcgaggacc gcatcggcag      840
gacctctatc cctatcgacc ccgagaaggt tgtaggcatc ctcgaatccg actaccagga      900
cgccactgcc cccaacgccg aggccgacga gagtgcgaac aagattgctg gccacttgat      960
tgagttcttc gagcacgagg tcgcccacgg ccgtctcccg aactccctcc ttcccctcca     1020
gtccggcatc ggcaacgtcg ccaacgccat catcggtggc ctcgacaact ccaacttccg     1080
caacctcaag gtctggactg aggttatcca ggacaccttc ctcgacctct tcgactcggg     1140
ccgcctcgac tttgccacgg ccacctctat ccgcttctcc ccgacggtt tccgccggtt     1200 ctacgacaac tgggaggcct actacggcaa gctcctcctc cgcagccagc aggtgtccaa     1260
ctcgcccgga tcatccgcc gccttggtgt cattgccatg aacaccccg tcgaggtcga     1320 catctacgcc cacgccaact ccacctgcgt catgggctcg cgcatgctca acggcctggg     1380
cggctccgcc gacttcctgc gctcctccaa gtactctatc atgcacaccc cgtccacccg     1440
cccctccaag accgacccgc acggcgtctc gtgcatcgtt cccatgtgca cccacatcga     1500
ccagactgag cacgacctcg acgtcatcgt caccgagcag ggcctggccg acgtgcgcgg     1560
cctgagcccc agggagaggg cccgcgtcat catcaagaag tgcgcccacc cggtctacca     1620
gcccatcctg acccactact ttgagaaggc cgagagcgac tgcctacgca agggctgggg     1680
ccacgagccc catctgctct tcaactcgtt tgacctgcac aaggccctcg tggagcacgg     1740
aagcatgcag aaggtcgggc agtgg                                           1765
```

<210> SEQ ID NO 3
<211> LENGTH: 1578
<212> TYPE: DNA
<213> ORGANISM: Acremonium chrysogenum

<400> SEQUENCE: 3

```
atggcatcac caatagcctc tgccgccctc aaggcgcgca ttcgccgccc ctcgatgctc       60
aagaagctgt gcaagcccca ggatttgatg catcacttcc ccaatggctc gtacattggc      120
tggtccggct tcaccggcgt cggctacccg aagaaaatgc cgacctacat ggccgatcac      180
gtcgagcaga acggcttca gggcaagctg aagtactcgc tattcgtggg cgcatcgtcg      240
ggtgctgaga cagagaatcg ctgggcgtcg ctcgacatga ttgataggag gaccccgcat      300
caggtcggca aggccatctc caagggcatc aatgagggca agatccactt cttcgacaag      360
catctctcca tgttccccgt ggaccttgta tacggctact acacaaagga tagaccccac      420
aacaagctgg acgtggtggt ggtggaggcc accgacatca agaggacgg aagcattgta      480 cccggagctt cagtcggcgc gacccccgag ctcatccaga tggccgataa gatcattatc      540
gaggtcaaca cctcactgcc ttcattcgag ggtctccacg acatcaccat gaccgacctg      600
cccccgctac ggaagcccta tctcgtcatg ggtgtcgagg accgcatcgg caggacctct      660
atccctatcg accccgagaa ggttgtaggc atcctcgaat ccgactacca ggacgccact      720
gcccccaacg ccgaggccga cgagagtgcg aacaagattg ctggccactt gattgagttc      780
ttcgagcacg aggtcgccca cggccgtctc ccgaactccc tccttcccct ccagtccggc      840
```

```
atcggcaacg tcgccaacgc catcatcggt ggcctcgaca actccaactt ccgcaacctc    900
aaggtctgga ctgaggttat ccaggacacc ttcctcgacc tcttcgactc gggccgcctc    960
gactttgcca cggccacctc tatccgcttc tccccgacg gtttccgccg gttctacgac    1020
aactgggagg cctactacgg caagctcctc ctccgcagcc agcaggtgtc caactcgccc    1080
gagatcatcc gccgccttgg tgtcattgcc atgaacaccc ccgtcgaggt cgacatctac    1140
gcccacgcca actccacctg cgtcatgggc tcgcgcatgc tcaacggcct gggcggctcc    1200
gccgacttcc tgcgctcctc caagtactct atcatgcaca ccccgtccac ccgcccctcc    1260
aagaccgacc cgcacggcgt ctcgtgcatc gttcccatgt gcacccacat cgaccagact    1320
gagcacgacc tcgacgtcat cgtcaccgag cagggcctgg ccgacgtgcg cggcctgagc    1380
cccagggaga gggcccgcgt catcatcaag aagtgcgccc accggtcta ccagcccatc    1440 ctgaccccact actttgagaa ggccgagagc gactgcctac gcaagggctg gggccacgag    1500
ccccatctgc tcttcaactc gtttgacctg cacaaggccc tcgtggagca cggaagcatg    1560
cagaaggtcg ggcagtgg                                                  1578

<210> SEQ ID NO 4
<211> LENGTH: 2570
<212> TYPE: DNA
<213> ORGANISM: Acremonium chrysogenum

<400> SEQUENCE: 4
gaagatcgca tttgggcgag tgggctaata atgcctgctg cctgcctgtg gacggtaaat    60
gaattaggtg gaatgtgtcg caaattgagg ggaatggccc ccttatcata taaagtgcca    120
atgcgatact atggcgtggc gtggggtcgc gtcggtgtcc ggccggtcga acggaggtcc    180
cggctatcaa taggcggtag gccggcattg aatcggttcc accgtattcc agacacccaa    240
ggaaggcccg ccaccccag ctccggcctg gggatagcgc cgagtggagc actcacgggg    300
gccgtgtttg actcgaagac gcgtcgtgat tggccagaac ttcatccccc tctgccaagt    360
attggttcac gggattcggc gacgtcaacg accccaccgg cccggattac ataaggtgca    420
ctgcagctac tacgtagtac tcgtacttgg gaaggaggga cccttggggt cggaggtttt    480
aaaggcaatg gcttcttcgc tggtccaccc aacctgactc tcactctccc ttttacctcg    540
ctcctctgat tattccctcg tctgcgtctg gatttcatct ctttccctc ccggccctt    600 tggatctctg ctctcccctc ctctctcccc cgcattggtg tgtaaaacca ctgtcccgcg    660
gcctcgcgac gagtgacgta ctgcaagccg aaacctcaca atcccttcct cacaatggca    720
tcaccaatag cctctgccgc cctcaaggcg cgcattcgcc gccctcgat gctcaagaag    780 ctgtgcaagc cccaggattt gatgcatcac ttccccaatg gctcgtacat ggctggtcc    840 ggcttcaccg cgctcggcta cccgaagtga gttccaccgt catcccgctc acagtaggc    900 gcagccggcc cgctgacagt ccccgacagg aaaatgccga cctacatggc cgatcacgtc    960
gagcagaacg gccttcaggg caagctgaag tactcgctat tcgtgggcgc atcgtcgggt    1020
gctgagacag agaatcgctg ggcgtcgctc gacatgattg ataggaggac cccgcatcag    1080
gtcggcaagg ccatctccaa gggcatcaat gagggcaaga tccacttctt cgacaagcat    1140
ctctccatgt tccccgtgga ccttgtatac gtacgtcaac gatgatccct tggaatgtgc    1200
atgtactacg agtacctggc gctaacatcc ggtcagggct actacacaaa ggatagaccc    1260
cacaacaagc tggacgtggt ggtggtggag gccaccgaca tcaaagagga cggaagcatt    1320
```

```
gtacccggag cttcagtcgg cgcgacccccc gagctcatcc agatggccga taaggtgagc    1380
aatttcgatt tctagcggag ggcgcagcag gacctgacat ctccctgtgc agatcattat    1440
cgaggtcaac acctcactgc cttcattcga gggtctccac gacatcacca tgaccgacct    1500
gcccccgcta cggaagccct atctcgtcat gggtgtcgag gaccgcatcg gcaggacctc    1560
tatccctatc gaccccgaga aggttgtagg catcctcgaa tccgactacc aggacgccac    1620
tgcccccaac gccgaggccg acgagagtgc gaacaagatt gctggccact tgattgagtt    1680
cttcgagcac gaggtcgccc acggccgtct cccgaactcc ctccttcccc tccagtccgg    1740
catcggcaac gtcgccaacg ccatcatcgg tggcctcgca aactccaact ccgcaacctt    1800
caaggtctgg actgaggtta tccaggacac cttcctcgac ctcttcgact cgggccgcct    1860
cgactttgcc acgccacct ctatccgctt ctcccccgac ggtttccgcc ggttctacga    1920
caactgggag gcctactacg gcaagctcct cctccgcagc cagcaggtgt ccaactcgcc    1980
cgagatcatc cgccgccttg gtgtcattgc catgaacacc cccgtcgagg tcgacatcta    2040
cgcccacgcc aactccacct gcgtcatggg ctcgcgcatg ctcaacggcc tgggcggctc    2100
cgccgacttc ctgcgctcct ccaagtactc tatcatgcac accccgtcca cccgcccctc    2160
caagaccgac ccgcacggcg tctcgtgcat cgttcccatg tgcacccaca tcgaccagac    2220
tgagcacgac ctcgacgtca tcgtcaccga gcagggcctg gccgacgtgc gcggcctgag    2280
ccccagggag agggcccgcg tcatcatcaa gaagtgcgcc cacccggtct accagcccat    2340
cctgacccac tactttgaga aggccgagag cgactgccta cgcaagggct ggggccacga    2400
gccccatctg ctcttcaact cgtttgacct gcacaaggcc ctcgtggagc acggaagcat    2460
gcagaaggtc gggcagtggt aagattggcg agacgggaga ggcgttgttg taggagttgg    2520
aactagaatc agatatacag cctttcatat atgtagataa tggagccatt                 2570

<210> SEQ ID NO 5
<211> LENGTH: 16032
<212> TYPE: DNA
<213> ORGANISM: Acremonium chrysogenum
<220> FEATURE:
<221> NAME/KEY: misc_feature
<222> LOCATION: (15909)..(15909)
<223> OTHER INFORMATION: n is a, c, g, or t

<400> SEQUENCE: 5
tacgtacata cgtcgcgggg ggtagacaat ggtgtggtgt acgtgtacaa ctacagtcag      60
acatggacgc aggaaacgca tcattgatac atgcacacgg ggcagcaaat ttagcctgtt     120
tcactacatg tacatagagg gtacactcca gagcatactg atgggagaaa aagggttcga     180
ttgctggtgg tttaacatag ccggcaaggg gaaaaaaaa aggggggcgga gaaggactga     240 ttcttcctgg cagacactcg acccttccgg cccccttgaac tgcttttact cccgcattcc     300
tccgcacgcc cgcccacagc ggcagatcag ccgaacctga tcgaccgatt taggtctgac    360
cattcttgtt gatcaagccc cgcagtcccc cctgcagata ctctccgtag gagatggccg    420
gcttgtcctt ggcggcatcc ttggcccat ccttggcggt cgcggggtcc cacggctgga     480
tggtgtcctc ccagcccagg ttgacgaaga agggcagtga ctggcgctcc tcgttgaccc    540
atttgacgcg gtggatcggg gccgggtagt agtcgtcggt gatatgggcc atgtagctgc    600
cgcagttgat gaggaagccc gtgtcgtcag cctggatgtc ctgccagccc tgcgggggtct    660 tgacctgcag attctgcacg tcggactggt acaacaccgt gatgagggac acgtcctcgt    720
gccactcgaa gctgagcttg gtgccgtcgt cggccgtctt gatggccggc tccgggtacg    780
```

-continued

```
ggtcgaggta cgggtaacgg atgagcacga ccgacgagag cgtcgtgtca cggcgggagt    840
ggcgggtgaa gaagtcctcg tcgcgaccta gggcgagagc gtagccgcgc agcaccgcgg    900
aggagaggcc gaagacgtcc cagtagtact tctcggcgaa ggcccggaac cccgggtgct    960
tcgcctcgtc cggccagacg ttgacctcgt gcataggggt gggctccttg attcgcggt    1020
ggtctgggct gaaggagggg ttcaggtagc agaacgattc gaccgccttc ttgcccggga   1080
tcggcaggta gtagcccgcc cggatctggg actcgtgctc cttgttgtag gcccggatgg   1140
cgagctgcca cttctcctcg tccgtgatgc tcatgtggaa tttgttcgtc tcgcgcgaga   1200
gccacggcag gtcgacaccg tggttcaccg cgtaaaagaa gcctgtgtcg cgcgatgcgg   1260
cgtcgatggc gcgagctacc tcgagcttct tctccttgtc atcgccgaat aggggcgaga   1320
catcgattcg ggggacgttg gccactggaa ctggaacgga acccatggtg acggtttgtc   1380
ctgcctggtg taagatgtga aagacgagat atgcgtgagt gacgatggcg aaggagaag   1440
cctcgaaaat cagaagagcg accaaaggga tattcaagta ttcgcccctc ttgaagctgt   1500
ttatacgggc ggctgggtgt gtgtatgtgt acttgagtac ctaccctcgtg tctcccgttg   1560
ctatacgata tgagcttccc cacgacgcgc ctttatggcc tgaccaaggt ctcgattatc   1620
cggctcctgc gggtgacact gccgaggggg gttacatacg gtccagcagc ggcgatggag   1680
tttggtccct gaagactgca tggcggggcc aagcgatgag gaacgccgtt acatgcatgt   1740
gcatgtagac gccgccaccc atgaggcccg gaacagtcta tcgaagctca gggattggcc   1800
cggcaactcg acgcccgtc gagcggctca ccggtagtcg acggcgtccg tcggaatctc    1860
gcgctgctgc gggccaccac ggcgatgggc cgtacacact gctactacgg tgtacaatgt   1920
atcatgtacc cgatcgacga ggaactcggg gtagaggtac cccgtacaat ccagtttctc   1980
aacccaatgg aaccacacat acggggtggc tttggttcac gttgcacttt aaactcgcag   2040
acgagggacc gacctgcagc gtggcccact tctgaagcct gcccagcttt ctgcaagacg   2100
cgggccatcg cgcttggccg aggagagaaa gggtatccat ggcgacaaag gcggtcctgg   2160
tgggttcggt gccggctttg gagttcactg gtctgggtgg gtggccagct ggatgcatgc   2220
attggcctgt atcaaaggtc cgggattccc caggagtata agacgttcgt gctgggagat   2280
ctagcgacgt gttgggaaat atcggccgta gagtgcgaaa aagaactggc ggaaatattt   2340
ctccttggac tcggtcacac tcagtcagta gtggactgcc agtctatcat acacctttga   2400
tatcaacatg actatcctta caggtgccga cgacgcctcg tcataccaca ggtatgtctt   2460
cacagcctct ggaaagcgca gttgggagct atctctaaca ttaccacatc aggcgcaatg   2520
gaagctctga tatcccaaaa ggtgccatcc accgcaacgg cttcgcagcc gcagcccctg   2580
actgctggat ccggtccgtg ctgtttccg tgcaccagat gctcaagagg ttcggaaacg    2640
gatctcacac cgtcgtggcg tcactcgtaa cttcatcaga gggatgccct tcaacttcgg   2700
cctggagggc catcccctcc gtcatccatc atatagaggg cggagacaac aacaacacag   2760
tcgcctctgc cgtggaacag gcggcgaatc tcctgaactc agaaggatcg ggacaggacc   2820
ttctgattcc catcggactc actgagctcg tcaagtcgga gctgattgac ctcctggtca   2880
tcttcgacga cgagacaaat aacatacgac tgccgcagga cttcccactt atcctgcgga   2940
tacatcagcg gcaagaccac tggcagctgt cagtccggta tccctcgccc cttttcgaca   3000
ccatggtcat cgacagcttt ctgagcgcac ttcacaacct gttgtccgcg gtgacaaaac   3060
cctcccagct cgtgcgcgac atcgagctgc tcccagaata ccaggtcgct cagctggaga   3120
```

```
agtggaacaa cacagacggc gactacccca ccgagaagcg gctacatcat ctgttcgagg   3180
aggcagcagt gcgtcgtccc caacacgttg ccctcatctg cggcgacaag cgcatcacct   3240
atgaggagtt gaatgctatg gcgaatcgcc tggcccacca tctggtatcc tcgggtatcc   3300
agactgagca gctcgtcggt ctcttcctcg acaagaccga gctcatgatc gctactattc   3360
tgggcatctg gaaatctggt gccgcgcatg tacctatcga ccctgggtac ccggacgagc   3420
gtgtcaagtt cgtcctgaat gatacgaagg cgcaagtggt cattgctagt cagaggcacg   3480
tcgatcgact gcgggctgag gctgttggcg gccagcatct tcgcatcatc ggtctcgaat   3540
ctctgttcga caaccttgct caacagacac aacactcacc agagacgtcg ggcaatttga   3600
cccatctgcc cctgaacagc aaacagcttg cgtacgtgac atacacctcg ggcaccacgg   3660
gcttcccgaa aggcatctac aaggagcaca caagcgtcgt taacagcatc accgatctgt   3720
ctgctcggta cggtgtggcc ggggaggacg acgaggtgat actcgtcttc tccgcctacg   3780
tcttcgagcc attcgtgcgc cagatgctca tggccctgac cacgggcaac tctctcgcca   3840
tcatcagcga cgaggacaag ttcgaccctg acacccttat tcccttcatc caaaaacaca   3900
aagtcactta catccacgcc acctcgtcag tgttgcagga gtacgacttc gggtcctgcc   3960
cctcgttgaa acgcatgatt ctggtgggag agaacttgac agagccgcgc tacgaggccc   4020
tgaggcagcg cttcaagtcg cgcatcctga atgaatatgg cttcaccgag tctgcgtttg   4080
tgacggcgct caacatattc gagcctacct cacagaggaa ggacatgagt ctgggaaggc   4140
cggtgcgcaa cgtcaagtgc tatatcttgg atgccaacct caagagagtc cccatcggtg   4200
ttacagggga gctgcacatc ggtggcttgg gtatatcccg ggggtacatg aataggagg    4260 agctcacaag gcagaagttc ctcccgaacc cctaccagac cgataaggag cgccaacggg   4320
gtgtcaactc aaccatgtac aagacaggag atctggcccg ctggctaccc agtggcgaag   4380
tcgagtatct cggccgtgcc gacttccaga tcaagctgcg cggcattcga attgagcccg   4440
gcgagatcga gtccactctc gccatgtatc ccggaatcag ggccagcatc gtcgtgtcaa   4500
agaagcttct cagtcagggg caggagacga tccaagacca ccttgtgggg tactatgttt   4560
gcgatgaggg ccacatcccc gagggtgacc tgctgagctt cctggagaag aagctacctc   4620
ggtacatggt cccgacgcgc cttgtccaac tggctcagat tccaaccaat atcaacggca   4680
aggcggatct gcgtgctctt cctgccgtcg aagtcgccgt agctcccacc cacaagcagg   4740
atggcgagcg aggaaaccag ctggagagcg acctggctgc catatggggc aacattttga   4800
gtgttcccgc tcaagacatt gggtctgaat ccaacttctt ccgcctgggt ggccacagta   4860
ttgcatgcat ccagctcatt gctcgtgtgc gacagcagct aggccagggg attaccctcg   4920
aggaggtctt ccagaccaag acgttgcgag ctatggctgc cctcttgtcg gaaaagtaca   4980
cgaaggcgtc gaatgggacg aacggagtga ccaacggcac tgctcacgtc aacggccacg   5040
cagcgaacgg ccatgtcagc gacagctacg tggccagcag tttgcagcaa ggctttgttt   5100
accattcact caagaacgaa ctgtccgagg cgtacaccat gcaatccatg atccactatg   5160
gtgtgcccct gaaacgggat atttaccaag cggcatggca gagggtacag ggggagcacc   5220
ctgcactgcg gcttcggttc acatgggagg ccgaagtgat gcagatcgtg acccgaaat    5280 ctgaactcga ctggcgtgtt gttgactgga ccgatgtttc gagccgggag aagcagctgg   5340
ttgcgctgga gcaactccaa acggaggacc ttgctaaggt ctaccatctc gataagggc    5400 cccttatgcg actataccct catcctgcttc cggactcaaa gtactcctgt ctgttcagct   5460
gccaccatgc cattctcgat gggtggagtc tgcccctgct cttcaacaat gtccaccagg   5520
```

-continued

```
cctacctcga tctcgtcgaa ggcactgctt cgcccgtcga gcaggacgct acctacctac   5580
tcggccagca gtacctgcag agccacaggg acgaccatct cgacttctgg gccgagcaga   5640
tcggcaggat cgaagagcgc tgcgacatga atgcgctgct gaatgaggcc agccgataca   5700
aggtgcccct ggccgactat gaccaagtcc gcgagcagag gcagcagacc atcagtctgc   5760
cctggaacaa ctccatggac gctggtgtgc gggaagaact ctccagtcgt ggcatcaccc   5820
ttcattccat tctacagacg gtctggcacc tggtcctcca ctcttatgga ggaggcaccc   5880
acacgatcac cggcaccacc atctccggcc gtcacctgcc cgtccccgga attgagcgct   5940
ctgttggtct cttcatcaac acactcccta tgatctttga tcacaccgtc tgccaggata   6000
tgacagcgct cgaggccatt gagcatgtcc aaggccaagt caacgccatg aactcccggg   6060
gcaacgtcga gctcggacgc atgagcaaga acgacctcaa gcacgggctc ttcgacaccc   6120
tcttcgtcct cgagaactac ccaaacctcg acacggagca gcgggagaag cacgaggaga   6180
agctcaagtt caccatcaag ggtggcacgg agaagctcag ttacccgctg ccgtgattg   6240
cccaagagga cggcgacagc ggatgctcgt ttacgcctctg ctatgcgggc gagctcttca   6300
cggatgagtc catccaggcg ctcctggaca ctgtccggga cccctgagt gatattctcg   6360
ggaacatcca tgccctatc cgcaacatgg agtacctctc ctcgaaccag acggcgcagc   6420
tcgacaagtg gaatgccacc gccttcgagt accccaacac cacactgcac gccatgttcg   6480
agtccgaggc gcagcagaag ccggacaagg tggccgtggt gtacgaggat atcaggctga   6540
cctaccgcga gctcaacagc cgtgccaatg ccctggcgtt ctacctcctc tcccaggcgg   6600
ctatccaacc gaacaagctg gtcgggctga tcatggacaa gagcgagcac atgatcacga   6660
gcatcctcgc ggtctggaaa acgggtggag cctacgtccc gatcgaccct cgatacctg   6720
accagcgtat ccagtatatc ctggaggata cggcggctct cgcagtcatc acggacagtc   6780
ctcatattga ccgtctgcgc agcatcacca acaaccgcct tcctgttatc cagtcggact   6840
tgctctcca actcccgccc agccagttc atcccgtctc aaactgcaag ccaagcgacc   6900
tcgcctacat catgtacaca tccggcacca ctggcaaccc caagggtgtc atggtgtagc   6960
accacggtgt agtgaatctg tgcgtttcac tctgccggct cttcggcctt cggaacacag   7020
atgacgaggt catcctctcg ttctcgaact acgtcttcga ccactttgtc gagcagatga   7080
cggatgccct tctcaacggt cagactcttg tggtcctcaa cgacgagatg cgtggcgaca   7140
aggagaggct ttacagatac atcgagacca accgcgtcac gtacctctcg ggacaccttt   7200
ccgtcatctc catgtacgag ttcgaccggt tccgcgacca cctgcggcgc gtggattgcg   7260
tcggcgaggc cttcagcgag ccggtattcg acaagatccg cgagacgttc ccgggtctca   7320
tcatcaacgg ttatggcccg actgaggtgt ctatcactac ccacaagcgc cctacccgt   7380
tcccggagcg ccgcacagac aagagcatcg gttgccagct ggacaacagc acgagctacg   7440
tcctcaacga tgacatgaag cgcgtgccca tcggggccgt gggagagctg taccttggtg   7500
gcgatggcgt cgctcgcgga taccacaacc ggccagacct gacggctgac cggttccctg   7560
ccaaccccctt ccagacggag caggagagac ttgagggccg aaatgcgcgt ctgtataaga   7620
ctggtgactt ggttcgctgg atccacaatg caaacggcga tggtgagatc gagtacctcg   7680
gccgcaacga cttccaggtc aagattcgag gccagagaat cgagctggga gagatcgagg   7740
ccgtgctttc atcctatccg ggcatcaaac aatccgtcgt cctggccaag gaccgcaaga   7800
atgacgggca gaagtacctc gtcggctact tcgtctcctc agcagggtcc ctgtccgccc   7860
```

```
aggccatccg ccgcttcatg ctcacgagcc tgcccgatta catggttcct gcgcagctgg   7920
tgcccatcgc caagttcccc gtcaccgtga gcgggaagct cgatgccaag gccttgcccg   7980
tgccagacga tacagtcgag gatgacattg tgccaccgcg taccgaggtt gagcgcatcc   8040
tagctgggat ctggtctgag ctgttggaga taccggtcga caggatcagc atctacagtg   8100
acttcttcag tctgggcggc gacagtctca agagtaccaa gctgtcctt gctgccacgc    8160 gggctctcgg tgtggccgtc agtgtccgca acttgttcag ccatccgact atcgaagcct   8220
tgtctcagtg gattatcagg ggttcgaacg aggtcaagga tgtggctgtg gtgaagggcg   8280
gtgccagtct tgatatcccc ctatccctg cccaggaaag actcatgttc atccacgagt     8340
tcggccatag cggcgaggat actggtgctt acaatgtgcc tttgcagctg cagcttcacc   8400
atgatgtctg tctcgagtcg cttgagaagg ctctgcggga tgtcgtctcg agacacgagg   8460
ctctccggac cttgatcacc aggacccaga agtcctccgt gcactgccag aagatcctcg   8520
acgccgaaga agcgcaaaag ctcttctctg ttgatgttct gcgcctgacc tcggagacgg   8580
agatgcaggg caggatggcc gagagtaccg cccacgcctt caagctcgac gaggaactcc   8640
cgattcatgt acgcctgtac caggttgtac gtgatggccg cacgctcagc tttgccagca   8700
tcgtctgcca ccatctggcg tttgacgcgt ggtcatggga tgtgttccag agggacttgg   8760
acgccttcta tgccgtccat acgaagcaca aggctgccgc caacctgcca accctccgcg   8820
tgcaatataa ggagtatgcg atagagcacc gccgggctct ccgcgctgag caacaccgtg   8880
ttctcgcgga ctactggctg cgcaagctca gtgacatgga ggcgtcttat ctggtccccg   8940
atcgccctcg accggcgcag tttgactata ccgggaacga tctccagttc tcaactactc   9000
ccgagaccag cgcgcagttg aaggagctgg ccaagcgcga gggttcaagc ctctacaccg   9060
ttgtggcggc ggcgtacttt ctgcttctct acgtgtacac caaccagcgg gatatcacga   9120
ttggtattcc cgttgcgcac cgtaaccatc cggactttga gtcggttgtc ggcttctttg   9180
tcaacttgct ccctctgcgg gtcaacgtgt ctcagtcgga cattcatgga cttatccagg   9240
cagtgcagaa agagcttgtc gatgcccaga tccatcagga cttgccattc caggagatca   9300
ccaagcttct tcatgtgcag cacgatccaa gccgccatcc ccttctccag gccgtgttca   9360
actgggaaaa cgtacccgcc aatgtccacg aggagcagct gcttcaggag tacaagccgc   9420
cctcgcctct gccttcggcg gccaagtttg atctcaacgt cacggtgaaa gagagcgtca   9480
attcgctcaa cgtcaacttc aactatccta ccagcctctt cgaggaggag accgttcagg   9540
ggttcatgga aaccttccat ctccttcttc gacaactggc ccacaacaag gctagcacaa   9600
gcctctcgaa gctgtcggtt gaagatggag tgttgaatcc agagccgact aaccttcagc   9660
cctcaagccg ggacagcgga aattcactcc atgggctctt cgaggacatc gtggcctcga   9720 cccccggaccg catcgcaatt gctgacggca ccaggagtct ctcgtactcc gaactcaacg   9780
agcgggcaaa ccagctggta catttgatca tctcttctgc cagtattgta gcagacgacc   9840
gcatcgctct tcttttggac aagagcatcg atatggtgat tgctctcctg gcagtttgga   9900
aggccggtgc cgcatatgtg ccccttgacc cgacatatcc gtcgcagagg actgagctca   9960
tcttggagga atctagtgcc aggacgctca tcaccactag aaagcacacg ccgaggggag  10020
gaacagtcgc aaatgttcca tccgtggtcc ttgacagccc cgagaccta gcctgcctca   10080 accagcagtc aaaggaaaac ccgacaacgt caacgcagaa accgtccgac ctcgcatatg  10140
tcatcttcac ctcgggaacc acaggcaagc ccaaggggga tctggtggag caccagagcg  10200
tagtccagct gcgcaattcc ctcatcgagc gatacttcgg cgagaccaac gggtctcacg  10260
```

```
ccgtgctctt cctgtccaac tacgtcttcg acttctctct tgaacagctc tgtctctcag   10320
tcttgggtgg aaacaagctc atcattccac cagaggaggg tctcacgcac gaggcattct   10380
acgacatcgg ccgcagggag aagctatcct atctcagcgg gacgccctcg gtgctgcagc   10440
agattgagct ctcccgtctg ccgcatcttc acatggtcac cgctgcgggc gaggagttcc   10500
acgctagtca gtttgagaag atgcgctccc agttcgcggg ccagatcaac aacgcctatg   10560
gtatcactga gacgaccgtg tacaacatca tcaccacgtt caagggcgat gccccctta   10620 ccaaggcact ctgccacggg atccccggaa gtcacgtcta cgtcctgaac gaccgacttc   10680
agcgtgttcc tttcaacgct gttggcgagc tctacttggg cggtgactgc cttgctcgcg   10740
ggtacctcaa ccaggatgcc ctgaccaacg agcgattcat ccccaaccct ttctacgagc   10800
cgaaacaggc aagtgacagt cgtccccaga gactctacaa gactggagat ctggtgcgct   10860
tccgtggacc ccaccatctc gagtatctcg gccgcaagga ccagcaggtc aagctgaggg   10920
gcttccgcat cgagctctcc gaggtgcggg atgccgtcct agccatctct gctgttaagg   10980
aggctgccgt catccccaag tatgacgagg atggctccga ttcacgaagg gtcagcgcca   11040
tcgtctgcta ctacacgctc aacgccggaa ctgtgtgcga agcatcgagt atccgtgacc   11100
acctgcacgc caaccttccc ccgtacatgg tcccaagtca gatccaccag ttggagggat   11160
ctctccccgt gaccgtcaat gggaagctcg acctgaacag gctctccaca actcaagtct   11220
cgcagccaga gctttacacc gctccacgaa attcgacaga ggaaaccttg tgccagcttt   11280
gggcatctct cctaggcgtc gaccactgcg gcattgacga cgacctgttt gcccgaggcg   11340
gcgacagcat ctcctctctc cgactagtgg gtgacatcta ccgcgcgcta ggacgcaagg   11400
tcaccgtcaa ggacatctac ctccaccgca gcgtccgagc cctaagcgaa aatgtcctga   11460
ccgaccagaa ggataagggt actctgccag cgtctcctcc cctccagcga gcggagcagg   11520
gccaggttga gggcgacgca ccgcttctcc ccatccagga ctggttcctt tccaagcccc   11580
tggataaccc cgcttactgg aaccactgct tcaccattcg aaccggggca ctctccgtcg   11640
aagggctccg gggtgctctg aagctgctgc aggagcgcca gcacgtgctg cgtctgagac   11700
tgcaacgccg ggacgaaggt cgccatgttc agacctttgc gcgtgactgc gcgcaacctc   11760
gcttgactgt gctagaccga cgaagcttcg aggacgcaga ggatgtacag gaggctctct   11820
gcgagatcca atctcatttc gacctcgaga atggaccct ctacacagtg gcgtacatcc   11880
acggttacga ggacggctcc gcccgagtgt ggtttgcctg ccatcacgtc atggtcgaca   11940
ctgtgagctg gaacattata ctgcaagacc tgcaggctct ctatcatgga gacagccttg   12000
gtcccaagag cagcagcgtg cagcagtggt cgctagctgt cagcgactac aaaatgccac   12060
tgtcggagag ggcgcattgg aatgtgctca ggaagacagt cgcccagagc ttcgagaccc   12120
tgcctatctg catgggcggc gtgctccagt gccaggagaa gttctcgagg gaaacgacaa   12180
cagctctgct ctccaaggcc tgccctgcct tggactccgg tatgcatgag atccttctca   12240
tggccgtggg ctccgcgctg cagaaggcgg caggggatgt ccctcaggtc gtcacgatag   12300
agggtcacgg gcgcgaagat actatcgacg caactctgga cgtcagccgg acagtcggct   12360
ggttcacgag catgtacccc ttcgagatcc ccaaagtgac cgaccccgct cagggcgtcg   12420
tcgatgtcaa ggaggcgatg cgtcgcgtgc cgaatagggg tgtcggttac ggtccagcct   12480
acggatacgg cggatcgtcg ctgcccgcgg tgagcttcaa ctaccttggt cgcctggacc   12540
aggcttcctc gggggctcaa agggactgga cgctggtcat ggatgaagac gagtatccgg   12600
```

```
tcggactgtg caccagcgct gaggactcgg gacgaagctc ctccatggtg gatttcacct    12660
tctctatctc tggcggccag cttgtcatgg atatgagtag cagctggggc cacggcgcag    12720
caaatgaatt cgttcgcaca gttcgtaaca cactagatga cttgatcaaa acaacgagca    12780
gcagggactt cagcgcacct ctgcctccgt cggatcagga gtccagcttc acccettatt    12840 ttgtcttcga agagggcgag cgacacggcg ctccgctctt cctgctccca cctggcgaag    12900
gcggagcgga gagctacttc cacaacattg tcaagggtct cccgaaccgc aatcttgtcg    12960
tgttcaacaa tcattaccgc gaggagaaga cgctccggac catcgaggcg ctggccgagt    13020
actacctgtc gcacatccga tccatccagc cggaggggcc ataccacatc ctcggctgga    13080
gtttcggagg catcctcggt ctcgaggcgg caaagcgatt gactggcgag ggtcacaaga    13140
ttgccacgct ggcacttatc gatccgtact ttgacatccc gtccgcgtcc aaggccatcg    13200
gccaacctga cgatgcctgc gtcttggacc ccatatacca cgtctaccac ccgtcgccgg    13260
agagcttcag gacggtgtca tctctcacta atcacatagc cctgttcaag gctaccgaga    13320
cgaatgacca gcatggcaat gccacgcagc aggccctgta tgagtggttt gccacgtgcc    13380
cttTgaacaa cctggacaag ttttTggcgg ccgacacgat caaggtggtt cctctggagg    13440
gtacacattt tacctgggtg caccacccgg agcaggtgcg ctcaatgtgc actatgctgg    13500
atgaatggct tgggtgaacg aggcagttgc tgtgagagaa tgagaatgag acacaaaacg    13560
cgggcggaag agagacttcc tcggacggcg ggtttccgcc gacgagtgat gacctggtcc    13620
caggggtctg gtgatatttt ctcctgaatg tgtgaggata ttagtggttt ttttctgccg    13680
ttagagacgt atttagtaag ctctggagtt tggagtcatt attttcctga atggtcttct    13740
tctgtagtaa taaactagca gagcggatta tatatatata tatatatatg tatttggctg    13800
gtattgctat gcgtgttcct atgtgaattg gtatatgtat aagtatgtct accttactgc    13860
atctgttaat tcttatgtac tgctacatga gttgctacgg ttattgcgac gtgatgcgtg    13920
tagtcgaagt tattgtacct attgcgtgta ctatgctccc ctcttctttc tactatatct    13980
cggtgtagta caaacaaaac gacgtagggg aagtggggaa gaagttgaac gagtatagac    14040
tccccgagca atgaatcagt acattatata tactgtttct tctctctcat gacttggtac    14100
gtgggaagtt cccaacatct aacctgtcca accctccgac cagaaagctg tccaacaatg    14160
tcgtccaacg ctcccagctc cccaagtatc atccatggca ccgaaggagc cgcatcatca    14220
actgaaaggc atcatctttg gactatcgca ccgggataat tctatacgac atccaagttg    14280
aattgtctga gcctcaggtc aggatcccag gcgtcaatct tggcagggga tagtgaaacc    14340
ttgaaacaag gcatgcgggc attgcgggca ttaggctcgc atagagaggg ggggttccag    14400
accgagagat atgcgtgcag ggccacgata ttggtgcgcc caattactag cataaaatac    14460
taatacaaat gcaggcaacc gaaggggatt attcataaat gccttgggtg catggcaact    14520
cgaaaagttg gggaatgtgg caggagcgcc caagcatatt cactcgtcaa gagtcgtcat    14580 caccacccc gcccaccttc ctatcttatt tcctcctcct tcagatcgta cgacactcat    14640
cttccctcgt ctcttttcca tcgtcgtcat caacaaaagt catctggctc gtctccatcc    14700
gaaacaccta ctagtagcta ttagtcactc actatgagac tctccttctt cgcgccaaac    14760
cgtacgataa aaagtccttt ggcctcgccc acgccgccag ggatccgccg tcacccgtca    14820
cgataaccta ccacgacatc cccctcaatg aggacaccgt ctccacggtt agggacgccg    14880
atgccgtctg cgccttcgta aatgactccc tctccgctca cgtcatcgag accctcgcca    14940
ggcagggtgt caaggccatc ctcctccgct gcgccggctt caatcacgtc gacctcgccg    15000
```

```
ccgccgcccg acacggcatc atggtcgcca acgtgccgtc gtactcgcca gaggccgtcg    15060
ccgagttcgc ggtagccctg atccagacac tcaaccgcaa cacccaccgc gcctacaacc    15120
gcgtgcgcga gggcaacttt gccctccacg gcctcctggg taagacactg cacggcaaga    15180
cggtcgggct agtgggcgtg gcaagatcg gcttggccac ggcgaggatc atgaagggct     15240
tcgggtgccg cgtccttgct agcgacccat ttccctcgcc tgcgtttgag gagtacggcc    15300
agtacaagga cctggacacg ttgctgtccg agtcggatat tgtcagcctc cactgtcccc    15360
tcatggacaa cacgcggcac atcatcaacg gcgacacaat cgccaagatg aaaaagggtg    15420
tcctcctcat caacacgtcc cgcggtggcc ttgtggacac ccgtgcagtc atcaaggccc    15480
tcaaaacaaa gcacattggc ggcgtagccc tcgacgtgta cgaggccgaa ggctcactgt    15540
tctacgacga ccactccggt gagattatcc acgacgatgt cctcatgcgc ctcatgacat    15600
tccccaacgt catcgtcacg ggacaccagg ccttcttcac cgaagaggcg ctcgaggaga    15660
ttgcacagtg cacgctgcgt aacctggagg agttcatcaa ggagggaaca tgcaagaact    15720
cgctgaccaa ggagcccgaa ttgaggtcca aggtccctga cccggtgcgc aatgtttaaa    15780
ttgatgtgga tgattgaatt ctatattctg gtatctctgt ctatgtacgg tcatctgaaa    15840
cttttgatgc tggttaaatg gtgagtcctg ctaacgccac acacaaacac acacacgcac    15900
acacacagng catattgaga cgaaactggg gaaagctaag tatcaataaa acacaaaacg    15960
aaatggacgg aaggatatct cccgctctag tatataaggc gtacgaaaac acccgttgta    16020
caaccgctta ag                                                       16032

<210> SEQ ID NO 6
<211> LENGTH: 5895
<212> TYPE: DNA
<213> ORGANISM: Acremonium chrysogenum

<400> SEQUENCE: 6
gatatctgag tggttgttcc gcgcgttacg gagtcatagc cggttgagtt cggccgaatc      60
tgccctctat gttgtgttta cgctcttcag gctttatgcg gaattacatg tgttttgcaa     120
gccacatttg ttttctatgt tacatcgttt cacgcgtcga tgggtcccgt taatagcaac     180
tagagtcttg gccgagccgc cgactggccg gacagtagat cccagtcccg ctcggtaaag     240
ggaacatact tgctcgcacc ggccggcagc cagaagaagc gatccttttc acttccaggg     300
accttgctgc ccatggagcg cgggtcgacc ccctcgtcgc ggagtggcac cttgttgtgt     360
ttatggttat ccgtgctcat gcctcccacc gtctcccgca ccctaatgaa gacaggaacg     420
gcgtaggagg gcaactctga ccgcaggagc gacgtcagcc gtgaccagtc caacgtgtct     480
ggggttgccg cgttcttcaa tgcgatggct gcgcagccgg ctcgcccgtc gtggttgggg     540
acctggacgc cgtagacatt ggcctcggca atgtctgcgt gtgagcccag gacttgtcct     600
acctcggtcg tggacacgtt ttctcctttc cagcggtatg tgtcgcctgg tattcacgtt     660
tagcattgtc actctgcgat tgtagcaggg ataacgtacc aagtcggtcg agaaagtacc     720
agtgaccgtc ggcatcgcgt cgaagtacca gtgaccgtcg catcgcgtc gaagagcatc     780 acccgtccgg aagtacagat cccccttctc aaacacattc tccaccagct tcttctgcgt     840
cgcctcctca gcatgccagt acccagccca ggctgaccgt gacgggagcc gcgccaggat     900
ctcaccgccc ctctcgtacg gcagtcgctc ggcaaagccc gtcttcggcg accgccagat     960
gtcacccgtc tccgggtcga tcctgacggg tacgtagtca ttgtgaaact tgcggcggag    1020
```

-continued

```
gagccaaccg tggtggccga cggcgccgag gccgaaacca ccgccgcggt agtgttttaa    1080
gagtgtcagg acgccttctg tgctggcgta gaattcaccg atgtccgata cgccgaagcg    1140
gtcctgttg tcgcttggtg tcaatcctat ggtttcgatg gggctggacc gaagtaaagg    1200
gggatcatac ctggaatttg gtccagagtt ccgggctgag tccgttcccc cagacgagac    1260
ggacgcggtg ctgacggtcc tttggtgagg ccggagcaga gagtaggtac cgaataagtt    1320
ccccgactgt acactcgtca ggagggcaaa caagtcgaag aagggtacca agggagagta    1380
gtggcttacc atagacaaat attgttgacc cgctctctat gcaatcgtcc cagaagcgag    1440
acaaggagaa cttgggcgca agagcaatgg atattccgct catcaagtcg ttcatggccg    1500
cgatgcccc cgttccgtgg tagagcggga tgcagtagta ggtgcggtca ccgttggggc    1560
ccggtttctg cccaaatgtc tttgcagca gtgaagcaga gggatagttc ctggccactg    1620
tgatgggtgc ggcctttggc aggccagtcg taccactttt gccgtgagaa tgtgcaactg    1680
gtgggtgaag tccgaggctt tactcaccta gtgtacatca aagcaaacgg tagcagcacc    1740
ttggtgtcct cgaagcaatc taccggtgcc ctgtgtgttt ctttccgggc aatgtcttcc    1800
ttcagcgtgc cggagagcat gatagcctcg acattgatat cccgaagccg ctcaccaact    1860
tcgtgaatgc gagaggaaca atcggacgca tcatcgtata tcagaaaccg cgagcgcgac    1920
aagcggacac agtgaaccag agcatcagag ccgagattgt aattgatgag ggcaggagca    1980
gcaccgatag acagtagacc catccagatg aacatcagct ccggcgagtt gtacagataa    2040
acaccgacgt gctgcccggc caccacgccc agatcgcgga agtagtggcc atactgacat    2100
gcgcgttggt acgtctgcgt ccacgagtac tcggggtgcc cgcgcgacca gatgcaaggt    2160
gcatcgccga ggcgggcagc ggcggcctcg aagaggaaga agccagatgc cttgcgctgc    2220
tcaacagctc tggcgaagtt ctgggccccc cgttcggcgc gggcgagctg gttgaggtcc    2280
ttggtgaggt gaagcttggc gtcgaggtag gcagcggcgg cggtgctggc ggcagcggcg    2340
ccagcgaggg ttagtaggcc gccgggtgcc attggggatt gccgttatgc tcccgtgtgt    2400
gcttgtgtct ttgcgagcga tgtccttgcc tccgagacat tggtgctggt gctggtggct    2460
ttgactgtct cggagaaggg tgtaagtgat cgtgcgatcg ggagtccaaa agttgaccaa    2520
acacggacac aaccagtatt gacgaatagt tgttgaagac tgctagcctc ggcacccaga    2580
agcttgggag acctgatggt gtggcgggtc tgtgggtttg ggcccttttg ggaggggcc    2640
aagggacatg gatggaggga gatcggcggc gatgttgcgg ccgcactaac aagaggtgtc    2700
cgtacgtccg gactccgtac ggtactgtac ggcgcccgtg gaaccaggca ctgaagattc    2760
aaggactgtt cctgtcggat atggccgcgc ccatgcgtgt ccaggttata gtctcgacta    2820
catacaaaca ttgtaccta cgtaaaagaa catggacagt aatacgctga ctcttggcta    2880
cgggatgata ttcactgccc aagaccgacg ccaagcagcg catactgtac gcataggcta    2940
cgtggtggaa acaccgtggc caactcatcc cttcgtacgg tacaacagcc ggacaggggg    3000
tgagggcggg tcggctccgc gggcagaagt gcttacagct aagagctag tggttaaggt    3060
tacatgtact aagcattggt ctggatcgaa tcagatgctg tgccttgact ggatcgagcg    3120
ggccggcccc ctgcgtctta atatagcaag tacccgtgac tatgtaagtt gtacatgtac    3180
atctgtgctg ccacaggagc gcctataatg tacccccacc ttgcacgaac attacattga    3240
tacttgcgtt tctccgtaca tgacagggg gtgatattac agtacatgct ccgccaagta    3300
atacaagaca cggaccatcg gaggcaaaca tttgtactgc agaatgatgc ctgatttagg    3360
cgcacagtct gcatacatgc catgccataa tgaggtcgtg tatccgtagt ctgtgctctg    3420
```

```
gatgactatg aattatgtct gaagttatta cttggcaaca acctgcttgc ccaactgggc    3480
aggtttcatt catgatggga ggatggagac gatgagtcta tccttggaca ctggcatgcg    3540
ccccgtcctt ggtgcagcta gattttcagc ttcgatgcac aggctccgcc cttgatacta    3600
cagcagagta catgccgaga caagaatctt caacgtcccc gatgcgcttt tgatatccac    3660
ccatgttttc atagtcgctg cgcggtatcg gacccgagtc gtctgtacac gtgggtagaa    3720
gttacgcgaa tgccacctca ccacgctgca ccatccatgc cgaggcaggc ttcgagattg    3780
caagtacgga ctacaataac atcaaatggc atggtgggat ttccgctgac cacctgccga    3840
cattacatgt tgtagtcttg accattcacg cggttaatcc cacctcgatg gaccccctctc   3900
```

-continued

```
ttcgacctcc gggggccga gttctagtcc gctaaccttc acggctacac cgtccctcgc    5820
gtctcaacta gccatataag tcctaggtaa agaggttaaa gtaggtagga aaggaacttg    5880
tggcttggcg gatcc                                                     5895

<210> SEQ ID NO 7
<211> LENGTH: 4623
<212> TYPE: DNA
<213> ORGANISM: Acremonium chrysogenum

<400> SEQUENCE: 7
tctagatacc ttgaaacttg aaactcttga cactcatgct ttgtgtttta aaaatttagc      60
aatttatagg gcaatttttc ttcttaaact cccgtagatt tattactcga tcggcggttc     120
cctaagtggc tataggagct gcggtagaga caggggcagc cgcggggaca gccgcctccg     180
ctgccgccgg cttatccctc cgcatgttga catagttccc gccaagccac tccctgaacg     240
tcgtgcgctc cgacgggatg cggacgttga aaccccactc cctcgactgc tgcacgttga     300
agctgaagtc gggcttcggc cgcaggaaga agacgctcga cgtgcggctg ctgccgacgc     360
gctggtcgcg cccgggagac ttgacccggt gcttgggcgc cttgaccttg ccgcccgtgg     420
ccagggtgcc gaccgcgccg cagaagacga ccatggcgcc ggggagcgtc gggaggtcga     480
cgaattctcc gtccacctcg cactgcaggc tcacgaagcc gttggcgcag gctgtctggt     540
gcacgagcgt gatggtcgat aggtcgtagt ggggtcccat gcggagggggt tcctcttcgg     600 cgacgcggtc ctccggcact tcggggaagt accgtaggcg gaggagggga tcgcactcga     660
cgaagtcatc aatgtcctcc ccggcgagcg gggcgcccac agagttgaga acggcgcgcg     720
cgacatcctt ggctgcgccg tacatgcggt cgaagtagtc ctgccagacg tcctcgaagc     780
cccggttcgg gaacaggttg ccgccgatgc ccatggagta gcacgtcgag tagtccgagt     840
acttgcccgt ctcggtgacg acggcggtgc tctcccactc gagggcagag aagccgcggc     900
gggcgttacg gtcggcgagc gtcacggccc tcttctcctc ctcgcttccg ttcttgaaaa     960
agtcaacgca cgtctcacgc gccgaggtgt ggtcgtcgtc gaccaggccg ctctcggtca    1020
agtagaagat acccttggtg gtgacggcct cggcgagctc ggtgaggacc ttgccgctct    1080
tgaggtcgtc gagacgaaag acggggacct tggaagtcat gttgatgctg tggttttgag    1140
cgatgacttg agaggagtag cgtggaggaa agttctgcaa gaggaattta aggattcaca    1200
agatcccagt gagaacgaaa cgttgtcaaa gcggtatata tatatctcaa accccacctc    1260
gtagcttacg ccgaggaact cctttttaga caactgctac ttagccgtaa gtgacgccct    1320
gcttcccctc agccttggcc gcacacgtca atgtagcatt gtaaacccac gagtgtcttg    1380
tgaagttttg tcaacgaatc ataagaagcc atcgagttct cttctcgttc ttggttcgca    1440
ggagaatatg tatcgtgcat ggtccctgat cgtcgagacc gccatggaat cgtgcaagcc    1500
ttaattctcc gtacaagctt ccccattcgg acaagattgc gatgatgtgg atgcgggctc    1560
ttttaataag gaccttctta accgatggtc cgagagtgcc taggacgggt ccatgtgcat    1620
acacgacgga ccctcgacct cctattagga gcatgaggga cgacaaaatg cgaacgacga    1680
tgcatcaaaa tgcactgcaa cgtcgagttg tgggctactc gccttctgat tcgcaagccc    1740
tcggcgagtc cacctactag tagcttggga ataaacagca agtttcgccg ccaaaagggc    1800
tgcccggcat ccgattcgat gccattgtac atcaagtcgg aaatggtgct ccgtttcccc    1860 ctgggggtgag agggcgaagg agtagttcga ccagtcgcag cgcacccaga gccgcaggtt    1920
ttatcggatg ttgcttcgat ccgatcgtat cccgcgcggc ctagatcttg ctaatacgag    1980
```

-continued

```
tcggagagtt actattccgg gcttatgcgg acgggccgcc gccgtcgatg ccggccaagg    2040
cttgtcgtgc atgatagatg ctgccgtcgg cccaagtggc ccgtctaaag ccggacccct    2100
ttcccccgag tctctcccg atcccgcacg gggccgtcac tttcgctgcc ctcgctcctt     2160
gtcataacct acctatattc tcatcccggc aaatgctgcg ggatagcctc acctacagcc    2220
acacgtcgcc caccatgtcg cctcagatcg ccaatcgctt cgaggcttcg ctagatgccc    2280
aagacatagc cagaatatcg ctcttcacac tggaatctgg cgtcatcctt cgcgatgtac    2340
ccgtggcata caaatcgtgg ggtcgcatga atgtctcaag ggataactgc gtcatcgtct    2400
gccacacctt gacgagcagc gcccatgtca cctcgtggtg gcccacactg tttggccaag    2460
gcagggcttt cgatacctct cgctacttca tcatctgcct aaattatctc gggagcccct    2520
ttgggagtgc tggaccatgt tcaccggacc ccgatgcaga aggccagcgc ccgtacgggg    2580
ccaagtttcc tcgcacgacg attcgagatg atgttcggta ggtaagcgca ccgatccagc    2640
ttgtctcaat atcgagtggt caggacaatc caggctaagc tttccgtgtc caaaagtatt    2700
catcgccagg tgctcgacag gttaggcgtc aggcaaattg ctgccgtagt cggcgcatcc    2760
atgggtggaa tgcacactct ggaatgggcc ttctttggtc ccgagtacgt gcgaaagatt    2820
gtgcccatcg cgacatcatg ccgtcagagc ggctggtgcg cagcttggtt cgagacacag    2880
aggcagtgca tctatgatga ccccaagtac ctggacgggg agtacgacgt agacgaccag    2940
cctgtccggg ggctcgaaac agcgcgcaag attgcgaatc tcacgtacaa gagcaaacct    3000
gcgatggacg agcgcttcca tatggctcca ggagtccaag ccggtgagtt tatagatgcc    3060
ttgccgtcgg tcgatgctca gagctaatca gaccgaaccc gctgctaggc cggaatatca    3120
gcagccagga tgcgaagaag gaaatcaacg gcacagacag cggcaacagc caccgtgctg    3180
gccagcccat tgaagccgta tcttcctatc tccggtacca ggcccagaag tttgccgcga    3240
gcttcgacgc caactgctac atcgccatga cactcaagtt cgacacccac gacatcagca    3300
gaggccgggc aggatcaatc ccggaggctc tggcaatgat tacacaacca gcgttgatca    3360
tttgcgccag gtcagacggt ctgtactcgt ttgacgagca cgttgagatg gggcgcagta    3420
tcccaaacag tcgtctttgc gtggtggaca cgaatgaggg tcatgacttc tttgtaatgg    3480
aagcggacaa ggttaatgat gccgtcagag gattcctcga tcagtcatta atgtgaggct    3540
atggaggtgt cagcctgccg gtgcgcgtac ttgccagggt gatcgatgta ctctcagata    3600
gtctccatgt gagtatggat ttcgctgttt ccgtcggat ataggcactc tcaggccatc     3660
tcgcagtagg tatcagaaca gcagctgagg ccttctcgga aagtaggttg tgtcaataga    3720
ttcataaagc gtcaaataaa gcccaaagtc gcagtagact catcgcatcg caagtctcag    3780
agggtcgact cggcagattc gaggcattgt agcacattgt cgaggcattg aggcggagac    3840
ttgacccatc caactcggcc agaggcagca ggcaaagcat ctcagcgtag gctccatgca    3900
aaacatgcgt ggctcaactc agcaagctca ttgccaacga ggtcaaagaa aatagaaggt    3960
agcggaggca ggcgggtatc gtagtaacac cgtccacata acacgggctc agcggagcaa    4020
cgtagtacct actcgtatag aggcaccgcg tcaggagagg tatcagaacc ctcatgattc    4080
tatcgccatg ctgctgcgaa cactaacaaa tgataaacaa gggcccatgc tgtgtgatga    4140
tgattcaagc aggttgtcgt ggtccaggtt tggtgcccga gccccgcaca gctgaagatg    4200
acgcgtctcg ctgtcgcgcc ttccacgacc cagaagttga tgtgcagaat gggcagtgag    4260
tgaacctggg cgggagtgat ggaaggtgcc taccctgtac aaccaactac gtcggtactc    4320
```

-continued

```
gtaggagcaa tagcgatgaa gcgtcgggag agaagtgtga attactctgg tacctggtac    4380
ttgatgcaac atagcacatt tcacccatca aagctaggtc ccgcggcctg ggagtggaat    4440
ggtgaaagac accgaggcaa atgcggcatg aatgaggaag cacggacgag tcgtggtttc    4500
acaagagaca ctctgaccga ccacaagatt cggcagtaca gtcacagcat caccatcggc    4560
agtcagacat gattcagagc caggtcttcg gcagagggaa ttagatacac ctcggcaccg    4620
gcg                                                                  4623
```

<210> SEQ ID NO 8
<211> LENGTH: 20
<212> TYPE: DNA
<213> ORGANISM: Artificial
<220> FEATURE:
<223> OTHER INFORMATION: oligonucleotide primer

<400> SEQUENCE: 8
tttgggcgag tgggctaata                                                  20

<210> SEQ ID NO 9
<211> LENGTH: 20
<212> TYPE: DNA
<213> ORGANISM: Artificial
<220> FEATURE:
<223> OTHER INFORMATION: oligonucleotide primer

<400> SEQUENCE: 9
caacaacgcc tctcccgtct                                                  20

<210> SEQ ID NO 10
<211> LENGTH: 18
<212> TYPE: DNA
<213> ORGANISM: Artificial
<220> FEATURE:
<223> OTHER INFORMATION: oligonucleotide primer

<400> SEQUENCE: 10
gcagagcgca gataccaa                                                    18

<210> SEQ ID NO 11
<211> LENGTH: 18
<212> TYPE: DNA
<213> ORGANISM: Artificial
<220> FEATURE:
<223> OTHER INFORMATION: oligonucleotide primer

<400> SEQUENCE: 11
cgtggactcc aacgtcaa                                                    18

<210> SEQ ID NO 12
<211> LENGTH: 18
<212> TYPE: DNA
<213> ORGANISM: Artificial
<220> FEATURE:
<223> OTHER INFORMATION: oligonucleotide primer

<400> SEQUENCE: 12
ttccatccag cacctcac                                                    18

<210> SEQ ID NO 13
<211> LENGTH: 18
<212> TYPE: DNA
<213> ORGANISM: Artificial
<220> FEATURE:
<223> OTHER INFORMATION: oligonucleotide primer

```
<400> SEQUENCE: 13
cttaatgcgc cgctacag                                          18

<210> SEQ ID NO 14
<211> LENGTH: 20
<212> TYPE: DNA
<213> ORGANISM: Artificial
<220> FEATURE:
<223> OTHER INFORMATION: oligonucleotide primer

<400> SEQUENCE: 14
atctgagtgg ttgttccgcg                                        20

<210> SEQ ID NO 15
<211> LENGTH: 20
<212> TYPE: DNA
<213> ORGANISM: Artificial
<220> FEATURE:
<223> OTHER INFORMATION: oligonucleotide primer

<400> SEQUENCE: 15
cgaggatgaa gacggtgaaa                                        20

<210> SEQ ID NO 16
<211> LENGTH: 25
<212> TYPE: DNA
<213> ORGANISM: Artificial
<220> FEATURE:
<223> OTHER INFORMATION: oligonucleotide primer

<400> SEQUENCE: 16
aggagaggcc gaagacgtcc cagta                                  25

<210> SEQ ID NO 17
<211> LENGTH: 22
<212> TYPE: DNA
<213> ORGANISM: Artificial
<220> FEATURE:
<223> OTHER INFORMATION: oligonucleotide primer

<400> SEQUENCE: 17
tttcgcttag ggctcggacg ct                                     22

<210> SEQ ID NO 18
<211> LENGTH: 20
<212> TYPE: DNA
<213> ORGANISM: Artificial
<220> FEATURE:
<223> OTHER INFORMATION: oligonucleotide primer

<400> SEQUENCE: 18
tcgggaggtg gaggaattct                                        20

<210> SEQ ID NO 19
<211> LENGTH: 20
<212> TYPE: DNA
<213> ORGANISM: Artificial
<220> FEATURE:
<223> OTHER INFORMATION: oligonucleotide primer

<400> SEQUENCE: 19
atcttgcgcg ctgtttcgag                                        20

<210> SEQ ID NO 20
```

```
-continued

<211> LENGTH: 20
<212> TYPE: DNA
<213> ORGANISM: Artificial
<220> FEATURE:
<223> OTHER INFORMATION: oligonucleotide primer

<400> SEQUENCE: 20
ggggcggagc ctatggaaaa                                               20

<210> SEQ ID NO 21
<211> LENGTH: 20
<212> TYPE: DNA
<213> ORGANISM: Artificial
<220> FEATURE:
<223> OTHER INFORMATION: oligonucleotide primer

<400> SEQUENCE: 21
tccagctcac cttgctccag                                               20
```